US012635932B2

(12) United States Patent　　(10) Patent No.:　US 12,635,932 B2
Gribble et al.　　　　　　　　　　(45) Date of Patent:　　May 26, 2026

(54) SYSTEMS AND METHODS FOR DISEASE DIAGNOSIS

(71) Applicant: RetiSpec Inc., Toronto (CA)

(72) Inventors: Adam James Gribble, Toronto (CA); Jared Lorne Westreich, Toronto (CA); Michael Frank Gunter Wood, Toronto (CA); Eliav Shaked, Toronto (CA); Alon Hazan, Toronto (CA)

(73) Assignee: RetiSpec Inc., Toronto (CA)

( * ) Notice: Subject to any disclaimer, the term of this patent is extended or adjusted under 35 U.S.C. 154(b) by 710 days.

(21) Appl. No.: 17/869,534

(22) Filed: Jul. 20, 2022

(65) Prior Publication Data

US 2023/0018494 A1　　Jan. 19, 2023

Related U.S. Application Data

(63) Continuation of application No. PCT/US2021/014821, filed on Jan. 23, 2021.
(Continued)

(51) Int. Cl.
A61B 5/00　　　　(2006.01)
A61B 3/00　　　　(2006.01)
(Continued)

(52) U.S. Cl.
CPC .......... A61B 5/4076 (2013.01); A61B 3/0008 (2013.01); A61B 3/12 (2013.01);
(Continued)

(58) Field of Classification Search
CPC ....... A61B 5/4076; A61B 3/0008; A61B 3/12; A61B 3/14; A61B 5/0075; A61B 5/7275;
(Continued)

(56) References Cited

U.S. PATENT DOCUMENTS

| 10,964,036 B2 | 3/2021 | Sylvestre et al. |
| 11,769,264 B2 | 9/2023 | Sylvestre et al. |
| | (Continued) | |

FOREIGN PATENT DOCUMENTS

| CA | 3088201 A1 | 7/2019 |
| JP | 2015-033397 A | 2/2015 |
| | (Continued) | |

OTHER PUBLICATIONS

Huebschman et al., "Hyperspectral Microscopy Imaging to Analyze Pathology Samples with Multi-Colors Reduces Time and Cost", Imaging, Manipulation and Analysis of Biomolecules, Cells, and Tissues VII, vol. 7182, pp. 290-200, Feb. 12, 2009.
(Continued)

*Primary Examiner* — Mohammed A Hasan
(74) *Attorney, Agent, or Firm* — Greenberg Traurig, LLP; Roman Fayerberg; Richard Brooks

(57)　　　　　　ABSTRACT

The present disclosure provides systems and methods for diagnosing disease. In some aspects, an imaging system is provided that includes a light source configured to illuminate a retina of the eye with light, one or more imaging devices configured to receive light returned from the retina to generate one or more spatial-spectral images of the retina, and a computing device configured to receive the one or more spatial-spectral images of the retina, evaluate the one or more spatial-spectral images, and identify one or more biomarkers indicative of a neurogenerative pathology.

26 Claims, 29 Drawing Sheets

Related U.S. Application Data

(60) Provisional application No. 63/059,349, filed on Jul. 31, 2020, provisional application No. 62/965,080, filed on Jan. 23, 2020.

(51) Int. Cl.

| | |
|---|---|
| *A61B 3/12* | (2006.01) |
| *A61B 3/14* | (2006.01) |
| *G06T 7/00* | (2017.01) |
| *G06T 7/11* | (2017.01) |
| *G06T 7/174* | (2017.01) |

(52) U.S. Cl.
CPC .............. *A61B 3/14* (2013.01); *A61B 5/0075* (2013.01); *A61B 5/7275* (2013.01); *G06T 7/0012* (2013.01); *G06T 7/11* (2017.01); *G06T 7/174* (2017.01); *A61B 2576/02* (2013.01); *G06T 2207/10152* (2013.01); *G06T 2207/30041* (2013.01); *G06T 2207/30101* (2013.01)

(58) Field of Classification Search
CPC . A61B 2576/02; A61B 5/4041; A61B 5/4058; A61B 5/4082; A61B 5/4088; G06T 7/0012; G06T 7/11; G06T 7/174; G06T 2207/10152; G06T 2207/30041; G06T 2207/30101; G01N 2333/4709; G01N 33/6896
USPC .......................................................... 351/221
See application file for complete search history.

(56) References Cited

U.S. PATENT DOCUMENTS

| | | | | |
|---|---|---|---|---|
| 2009/0225277 | A1* | 9/2009 | Gil ........................ | G01J 3/0256 351/246 |
| 2012/0081695 | A1* | 4/2012 | Majumdar ........... | G01J 3/2823 356/72 |
| 2018/0042483 | A1* | 2/2018 | Bardhan ............... | G01J 3/2823 |
| 2018/0317832 | A1* | 11/2018 | Scott ........................ | A61B 3/14 |
| 2019/0107439 | A1* | 4/2019 | Vince ..................... | G01J 3/027 |

| | | | | |
|---|---|---|---|---|
| 2022/0084210 | A1* | 3/2022 | Manivannan ........ | G06V 10/421 |
| 2022/0157470 | A1 | 5/2022 | Sylvestre et al. | |
| 2023/0394689 | A1 | 12/2023 | Sylvestre et al. | |

FOREIGN PATENT DOCUMENTS

| | | |
|---|---|---|
| JP | 2016-512133 A | 4/2016 |
| JP | 2016-524494 A | 8/2016 |
| JP | 2019-054994 A | 4/2019 |
| JP | 2019-118814 A | 7/2019 |
| JP | 2019-180693 A | 10/2019 |
| WO | 2012177997 A1 | 12/2012 |
| WO | 2019100169 A1 | 5/2019 |
| WO | 2019136513 A1 | 7/2019 |

OTHER PUBLICATIONS

Sharafi et al., "Chapter 5: Article 2: Hyperspectral Retinal Biomarkers of Atherosclerosis, Investigation of the Retinal Biomarkers of Alzheimer's Disease and Atherosclerosis Using Hyperspectral Images," pp. 65-80, Nov. 19, 2019, Retrieved from the Internet: https://publications.polymtl.ca/4041/1 /2019_SayedMehranSharafi, retrieved on Feb. 12, 2024.

Supplementary European Search Report in EP Application No. 21743828.2 dated Feb. 28, 2024.

Hadoux et al. "Non-invasive in vivo hyperspectral imaging of the retina for potential biomarker use in Alzheimer's disease. "Nature communication 10.1 (2019): 1-12. Sep. 17, 2019 <https://www.nature.com/articles/s41467-019-12242-1>.

Sharafi et al. "Vascular retinal biomarkers improves the detection of the likely cerebral amyloid status from hyperspectral retinal images". Alzheimer's & Dementia: Translational Research & Clinical Interventions 5 (2019) 610-617. Jan. 1, 2019 <https://alz-journals.onlinelibrary.wiley.com/doi/10.1016/j.trci.2019.09.006>.

Gramatikov. "Modern technologies for retinal scanning and imaging: an introduction for the biomedical engineer". Biomedical engineering online 13.1 (2014): 1-35. Apr. 29, 2014 <https://www.ncbi.nlm.nih.gov/pmc/articles/PMC4022984/>.

Koronyo et al. "Retinal amyloid pathology and proof-of-concept imaging trial in Alzheimer's disease". JCI insight 2.16 (2017). Aug. 17, 2017 <https://insight.jci.org/articles/view/93621>.

International Search Report; PCT/US2021/014821 Dated: Apr. 21, 2021; By: Authorized Officer Blaine R. Copenheaver.

* cited by examiner

Spectrometer
Image line spectra through fundus

Color Fundus Camera
Determine health of eye and provide reference image

Hyperspectral Camera
Full spectral image

Spectrometer Mean Results

Error bars represent standard error

Disc

310 (AB−)

312 (AB+)

Optical Density

Wavelength (nm)

Optical density spectra of disc of positive and negative amyloid status individuals

Fovea

314 (AB−)

316 (AB+)

Optical Density

Wavelength (nm)

Optical density spectra of fovea of positive and negative amyloid status individuals Ratio significance of reflectance spectrum 500 — Provide retinal image mosaic from all patient acquisitions 502 — spectral – Spatial CNN 504 — Generate heatmap describing disease signal predicted probability 506 — Evaluate heatmap and output final score indicative of pathology Tau Amyloid Spectral-Vessel AI Approach
```
700                  702                704                 706
Apply deep     →   Develop         →  Extract         →   Use AI to identify
learning           projection          accurate            amyloid markers along
model to           from HSI            vessel              the vessels
segment            to RGB              segmentation
vessels in
RGB images
```
FIG. 17A
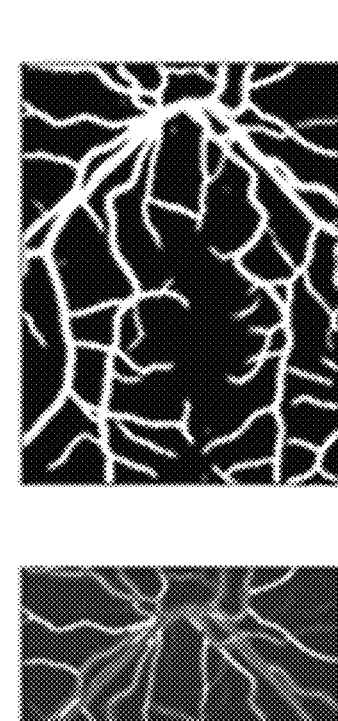
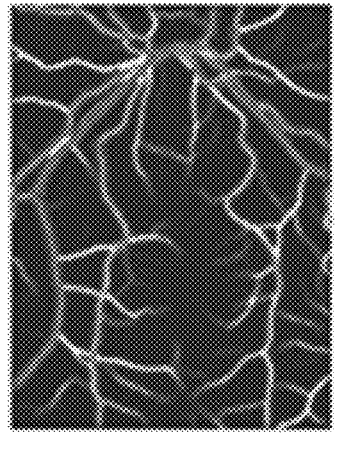
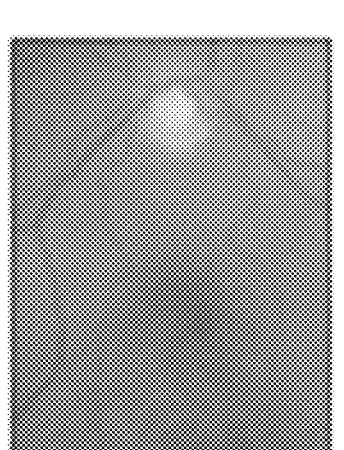
FIG. 17B

SYSTEMS AND METHODS FOR DISEASE DIAGNOSIS

RELATED APPLICATIONS

This application is a continuation application of PCT International Patent Application No. PCT/US2021/014821, filed on Jan. 23, 2021, which claims the benefit of and priority to U.S. Provisional Application Ser. No. 62/965,080, filed on Jan. 23, 2020, and U.S. Provisional Application Ser. No. 63/059,349, filed on Jul. 31, 2020, all of which are incorporated herein by reference in their entireties.

FIELD

This disclosure relates to systems and methods for diagnosing disease, for example, Alzheimer's disease, by using optical techniques to measure and analyze properties of the eye.

BACKGROUND

Alzheimer's disease (AD) is a debilitating and fatal neurodegenerative disease. Confirmation of the disease is commonly performed post-mortem. Some existing conventional systems for diagnosis involve either highly invasive procedures or imaging devices that are often inaccessible or inappropriate due to cost, complexity, or the use of harmful radioactive tracers.

There is a need for a non-invasive detection system that is easily operable and accessible by clinicians for screening patient populations for early detection of AD-associated pathologies, diagnosis, and tracking of patient response to preventative or treatment interventions.

The optic nerve and retina are developmental outgrowths of the brain and many conditions affecting the brain manifest in these structures as well, such as amyloid beta ($A\beta$) protein accumulation, changes to the structure of retinal layers, and other changes in chemical composition, structure, and function. The eye is easily examined using a variety of non-invasive light-based techniques to identify these physical changes, making optical analysis highly suited for the present needs.

SUMMARY

The present disclosure provides systems and methods for diagnosing disease. In some aspects, an imaging system is provided that includes a light source configured to illuminate a retina of the eye with light, one or more imaging devices configured to receive light returned from the retina to generate one or more spatial-spectral images of the retina, and a computing device configured to receive the one or more spatial-spectral images of the retina, evaluate the one or more spatial-spectral images, and identify one or more biomarkers indicative of a neurogenerative pathology. In some embodiments, the one or more imaging devices comprise a spectral sensor. For example, the spectral sensor can be a hyperspectral sensor or multispectral sensor.

In some embodiments, the neurogenerative pathology is selected from the group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), cerebral amyloid angiopathy (CAA). In some embodiments, the biomarkers comprise Amyloid or Tau protein formations.

In some embodiments, the system can further include a retinal viewing device, wherein the one or more imaging devices and the light source are integrated into the retinal viewing device. For example, the retinal viewing device is a fundus camera. In some embodiments, the one or more spatial-spectral images comprise spectral images of multiple retinal regions. In some embodiments, for each of the multiple retinal regions, the one or more spatial-spectral images comprise spectral images at multiple wavelength ranges. The spectral images can include spatial information about a corresponding retinal region. the spatial information can comprise texture, formations and patterns in the corresponding retinal region. In some embodiments, the evaluation of the one or more spatial-spectral images uses a pixel-wise analysis of the images.

In some embodiments, an imaging system can be provided that includes a light source configured to illuminate a retina of the eye with light, one or more imaging devices configured to receive light returned from the retina to generate at least one spectral image and at least one spatial image of the retina, and a computing device configured to receive the at least one spectral image and at least one spatial image of the retina, evaluate the images, and identify one or more biomarkers indicative of a neurogenerative disease. In some embodiments, the one or more imaging devices comprises a spatial camera configured to generate the at least one spatial image and a hyperspectral camera configured to generate the at least one spectral image. In some embodiments, the one or more imaging devices comprises a hyperspectral camera configured to generate an image that includes the spectral image and the spatial image. In some embodiments, the biomarkers comprise Amyloid or Tau protein formations.

In some embodiments, a method for diagnosing a neurogenerative disease is provided, and can include illuminating a retina of an eye with light with a light source, generating at least one spatial-spectral image by one or more imaging devices, the one or more imaging devices configured to receive light returned from the retina, evaluating the at least one spatial-spectral image, the image being evaluated by a computing device configured to receive the at least one spatial-spectral image from the one or more imaging devices and identifying one or more biomarkers indicative of a neurogenerative disease.

In some embodiments, the evaluation of the at least one spatial-spectral image uses a pixel-wise analysis of the image. In some embodiments, the one or more imaging devices comprise a spectral sensor. In some embodiments, the spectral sensor comprises a hyperspectral sensor or multispectral sensor. In some embodiments, the neurogenerative pathology is selected from the group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), cerebral amyloid angiopathy (CAA). In some embodiments, the biomarkers comprise Amyloid or Tau protein formations.

In some embodiments, a method for diagnosing a neurogenerative disease is provided that includes obtaining, by a computer device, a retinal image mosaic comprising a plurality of spatial-spectral images from one or more regions of a retina, analyzing, by the computing device, the plurality of spatial-spectral images to identify one or more biomarkers indicative of a neurogenerative pathology, and generating, by the computing device, a digital representation indicative of a presence or absence of the biomarkers in the one or more regions of a retina.

In some embodiments, the can also comprise predicting a probability of the neurogenerative pathology from the digital representation. In some embodiments, the digital representation is a heat map overlaid on the retinal image mosaic. In some embodiments, analyzing the plurality of spatial-spectral images comprises using a pixel-wise analysis of each image. In some embodiments, the plurality of spatial-spectral images are generated by one or more imaging devices comprise a spectral sensor. For example, the spectral sensor can comprise a hyperspectral sensor or multispectral sensor. In some embodiments, the neurogenerative pathology is selected from the group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), cerebral amyloid angiopathy (CAA). In some embodiments, the biomarkers comprise Amyloid or Tau protein formations.

In some embodiments, an imaging system is provided that includes a light source configured to illuminate a retina of the eye with light, one or more imaging devices configured to receive light returned from the retina to generate one or more spatial-spectral images of the retina, and a computing device. The computing device can be configured to obtain a retinal image mosaic comprising the one or more spatial-spectral images from one or more regions of a retina, analyze the one or more spatial-spectral images to identify one or more biomarkers indicative of a neurogenerative pathology, and generate a digital representation indicative of a presence or absence of the biomarkers in the one or more regions of a retina.

In some embodiments, any of the systems or methods can be used such that one or more vessels of a retina are segmented, and the biomarkers are identified along the one or more vessels or the vessel walls.

BRIEF DESCRIPTION OF DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 17A is an exemplary flowchart illustrating a method for analyzing vessels of the retina;

FIG. 17B illustrates exemplary representations of images relating to the method in FIG. 17A;

Figure 1A:
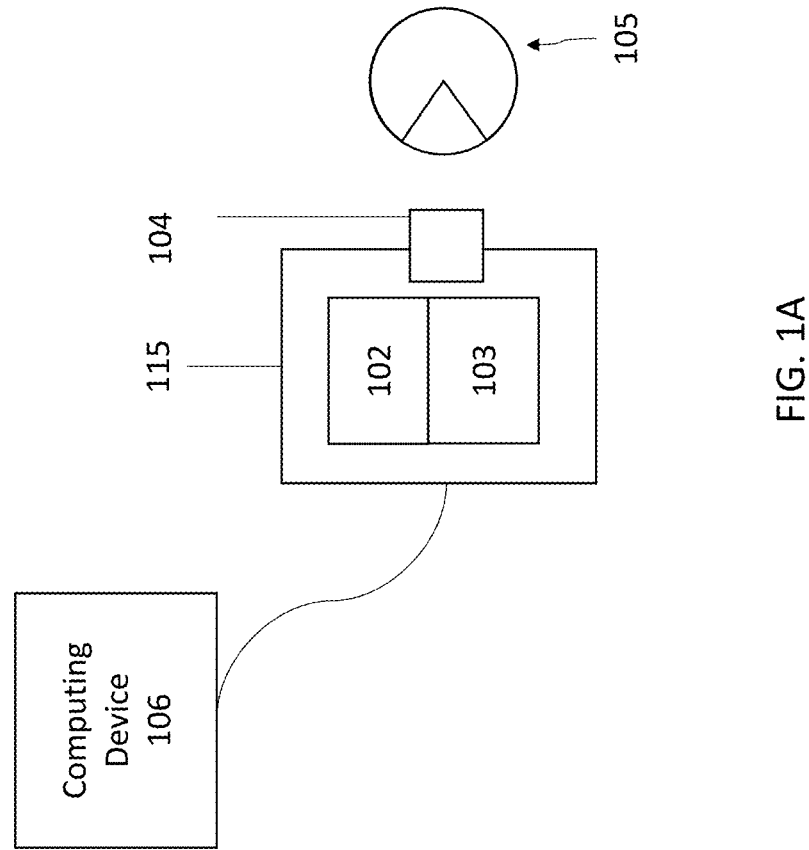
FIG. 1A shows a schematic of an exemplary embodiment of a system with a light source and an imaging device.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments. Embodiment examples are described as follows with reference to the figures. Identical, similar, or identically acting elements in the various figures are identified with identical reference numbers and a repeated description of these elements is omitted in part to avoid redundancies.

The instant methods and systems can be used to detect the existence of one or more Alzheimer's disease (AD) associated pathologies or pathologies associated with other neurogenerative diseases, such as, for example, Parkinson's disease (PD), amyotrophic lateral sclerosis (ALS), multiple sclerosis, Prion disease, Motor neurone diseases (MND), Huntington's disease (HD), Spinocerebellar ataxia (SCA), Spinal muscular atrophy (SMA), cerebral amyloid angiopathy (CAA), other forms of dementia, and similar diseases of the brain or the nervous system. In some embodiment, the systems and methods of the present disclosure can be used to detect protein aggregates of Aβ, tau, phosphorylated tau and other neuronal proteins indicative of a neurogenerative disease, in particular Alzheimer's disease. In some embodiments, the detected protein aggregates can include at least one of Tau neurofibrillary tangles, Amyloid Beta deposits or plagues, soluble Amyloid Beta aggregates, or Amyloid precursor protein. These detected proteins can be indicative of a pathology in the brain as they can be correlated to brain amyloid and/or brain tau. The system allows for the identification of at-risk populations, diagnosis, and tracking of patient response to treatments.

In some embodiments, the systems and method of the present disclosure may detect biomarkers indicative of tau pathologies or tauopathies, including, without limitation, total (T-tau), Tau PET, and phosphorylated tau (P-tau). In some embodiments, the biomarkers indicative of a Tauopathy include, but are not limited to, phosphorylated paired helical filament tau (pTau), Early Tau phosphorylation, Late Tau phosphorylation, pTau181, pTau217, pTau231, total Tau, Plasma AB 42/40, Neurofibrillary tangles (NFTs) and aggregation of misfolded tau protein. In some embodiments, neurofilament light protein (NFL), neurofilaments (NFs) or abnormal/elevated neurofilament light protein (NFL) concentration can be detected. In some embodiments, surrogate markers of a neurodegenerative disorder or neuronal injury can be detected, for example, retinal and optic nerve volume loss or other changes, degeneration within the neurosensory retina, and optic disc axonal injury. In some embodiments, an inflammatory response or neuroinflammation may be detected and may be indicative of neurogenerative disease. In some embodiments, such inflammatory response may be detected in the retinal tissue. Examples of such responses include, but are not limited to, retinal microglia activation, degenerating ganglion cells (ganglion neuron degeneration) or astrocyte activation. Other protein aggregates or biomarkers useful in the methods and systems of the present disclosure include alpha synuclein and TDP43 (TAR DNA binding protein-43) and others described, for example, in Biomarkers for tau pathology (Molecular and Cellular Neuroscience, Volume 97, June 2019, Pages 18-33), incorporated herein by reference in its entirety. In some embodiments, the systems and methods of the present disclosure can be used to detect the presence or absence of protein aggregates or biomarkers indicative of one or more neurogenerative diseases in the patient's eye tissue, brain tissue, tissues of the central nervous system, peripheral nervous system, or in the cerebrospinal fluid (CSF) or any other tissue where such formations or their biomarkers occur. In some embodiments, the systems and methods of the present disclosure detect protein aggregates or biomarkers indicative of one or more neurogenerative diseases without using a dye or ligand. In some embodiments, dyes or ligands may be used to assist the presently disclosed methods and systems. In some embodiments, the results of the optical tests can be confirmed using an anatomic MRI, FDG PET, plasma test, and/or CSF total Tau.

In some embodiments, a non-invasive ocular light-based detection system is provided for detecting neurogenerative disease-associated pathologies in the eye. The system can be used for optical examination of part of the fundus, such as the retina to look for signs of AD-associated pathologies in the patient's eye tissue, brain tissue, tissues of the central nervous system, in cerebrospinal fluid (CSF or any other tissue where such formations or their biomarkers occur. The device is a light-based tool that provides an accessible and non-invasive procedure for identifying at-risk populations of Alzheimer's disease, diagnosis, and tracking treatment and intervention efficacy. In some embodiments, disease can be detected by first determining particular regions of the tissue to be interrogated using a first imaging modality. This detected information can be used to guide a second imaging modality to determine the existence of one or more AD-associated pathologies, including but not limited to protein aggregates, the protein aggregates including at least one of: Tau neurofibrillary tangles, Amyloid Beta deposits, soluble Amyloid Beta aggregates, or Amyloid precursor protein. For example, a first imaging modality may be used to identify the locations of blood vessels in the retina and a second imaging modality can then be used to analyze the spectral features of the blood vessels where the AD-associated pathologies may be more likely to be evident. The system allows for the identification of at-risk populations, diagnosis, and tracking of patient response to treatments.

Imaging Systems

In some embodiments, a system for diagnosing disease, such as Alzheimer's disease, includes a retinal viewing device, a light source for illuminating the retina, and an imaging device for producing a measurement or an image of the retina from light reflected from the light source by the retina and received by the retinal viewing device. The retinal viewing device may be any optical assembly configured to collect light reflected from the retina and/or other parts of the fundus of an eye, such as a configuration of one or more lenses. In some embodiments, the system may further include a computer system for analyzing the imaging data.

A retina imaging system configured to capture one or more images of the retina for pathology detection can include an imaging device 102 and a light source 103, as shown in FIG. 1A. In some embodiments, the imaging device can be in the form of a hyperspectral or multispectral camera configured to take one or more spatial-spectral images of the retina, as will be discussed in more detail below. In some embodiments, the imaging device and the light source can be placed inside a housing 115 with an optical element 104 configured to direct light from the light source to the retina of an eye 105, and light reflected from the retina to the imaging device. In some embodiments, the housing 115 can be a handheld housing. In some embodiments, the imaging device 102, the light source 103 or both can be in communication with a computing device 106 for obtaining and analyzing the pathology data.

Figure 1B:
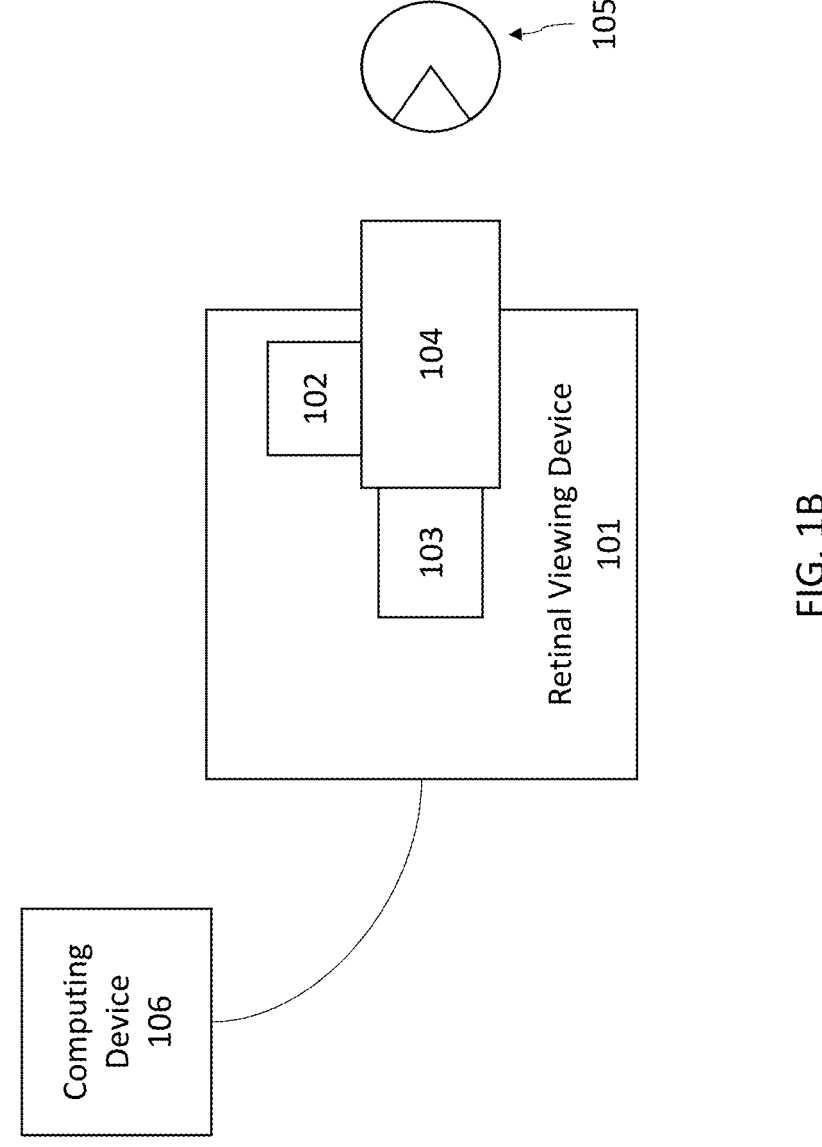
FIG. 1B shows a schematic of an exemplary embodiment of a system with a light source and an imaging device contained within the retinal viewing device.

In some embodiments as shown in FIG. 1B, the imaging device 102 and light source 103 can be integrated (with or without the housing 115) into a retinal viewing device 101 (for example, a fundus camera) with the optical element 104 configured to direct light from the light source to the retina of an eye 105, and light reflected from the retina to the imaging device. Output from the imaging device is coupled to a computing device 106. The computing device may also be configured to control the settings of one or more of the imaging devices, including image settings as well as scanning and positioning settings. In some embodiments, 102 and 103 can be integrated into a retinal viewing device 101, such as a fundus camera.

Figure 1C:
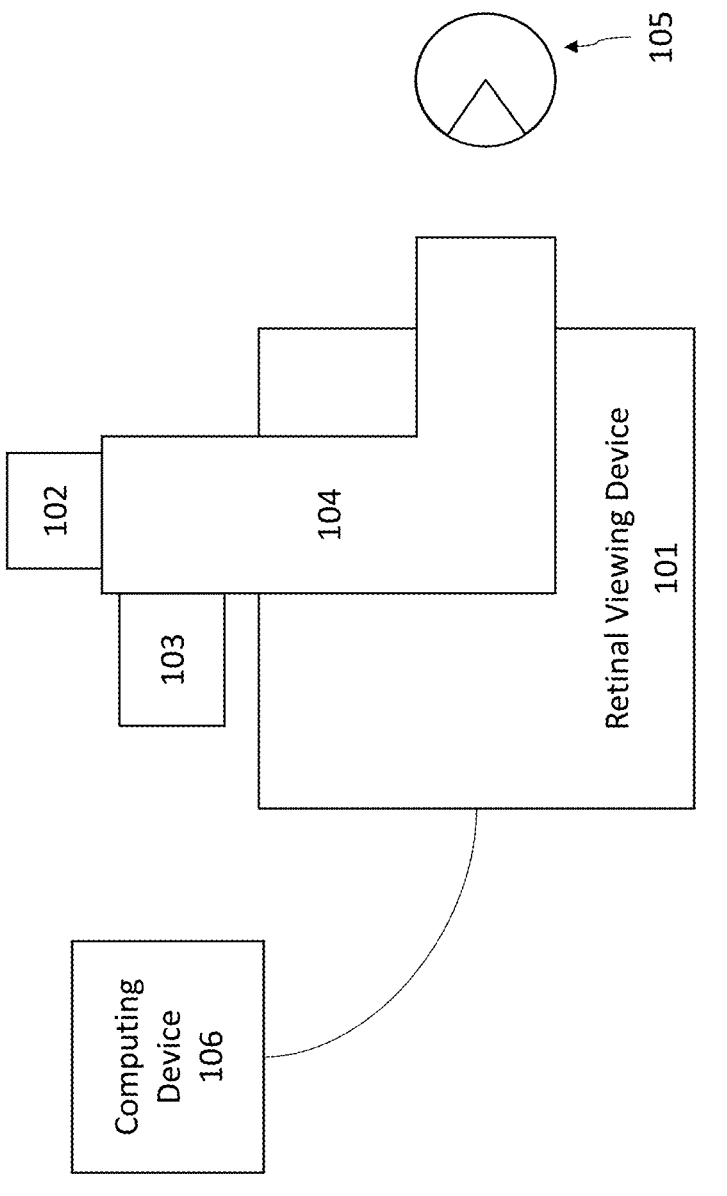
FIG. 1C shows a schematic of an exemplary embodiment of the system with a light source and imaging device external to the retinal viewing device.
Figure 1D:
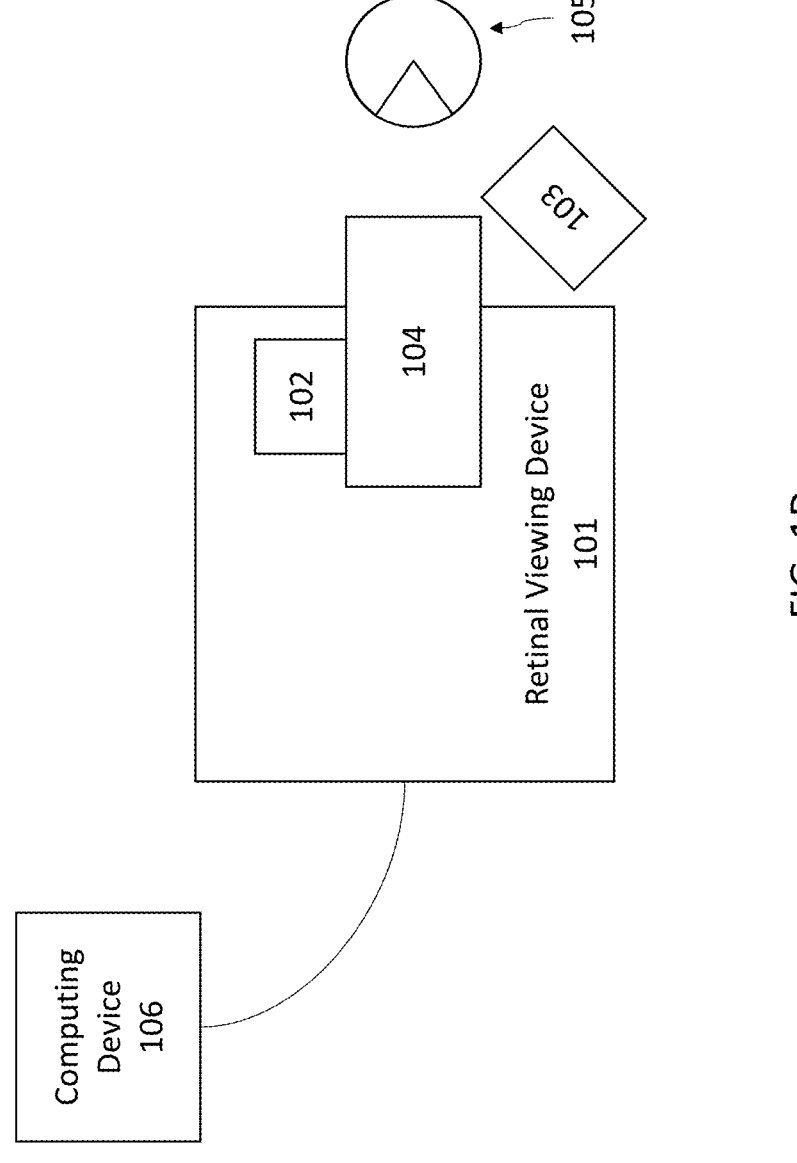
FIG. 1D shows an exemplary embodiment of the system with an imaging device contained within the retinal viewing device and a light source independent of the retinal viewing device.

FIG. 1C shows an embodiment in which the imaging device 102 and light source 103 are external to the retinal viewing device 101, with optical elements 104 configured to couple with the imaging device and light source through external ports. FIG. 1D shows an embodiment in which the light source 103 is independent from the retinal viewing device 101.

Figure 1E:
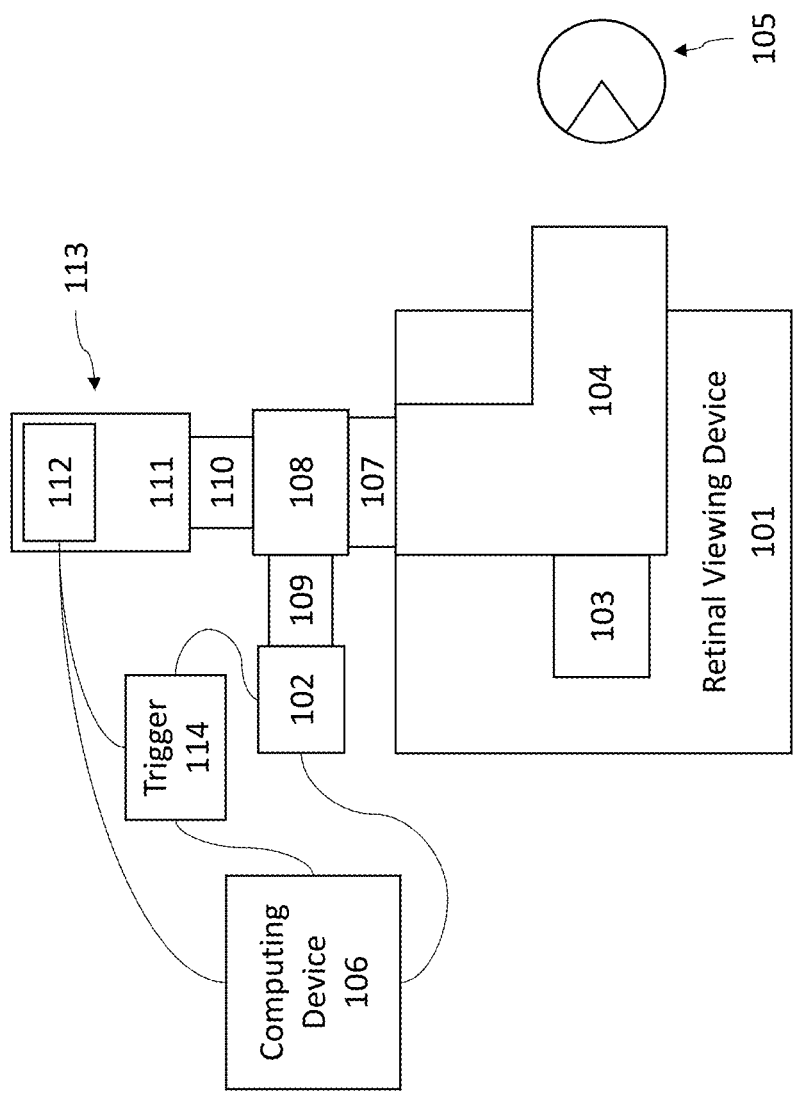
FIG. 1E shows a more detailed schematic of an exemplary embodiment of the system.
Figure 2A:
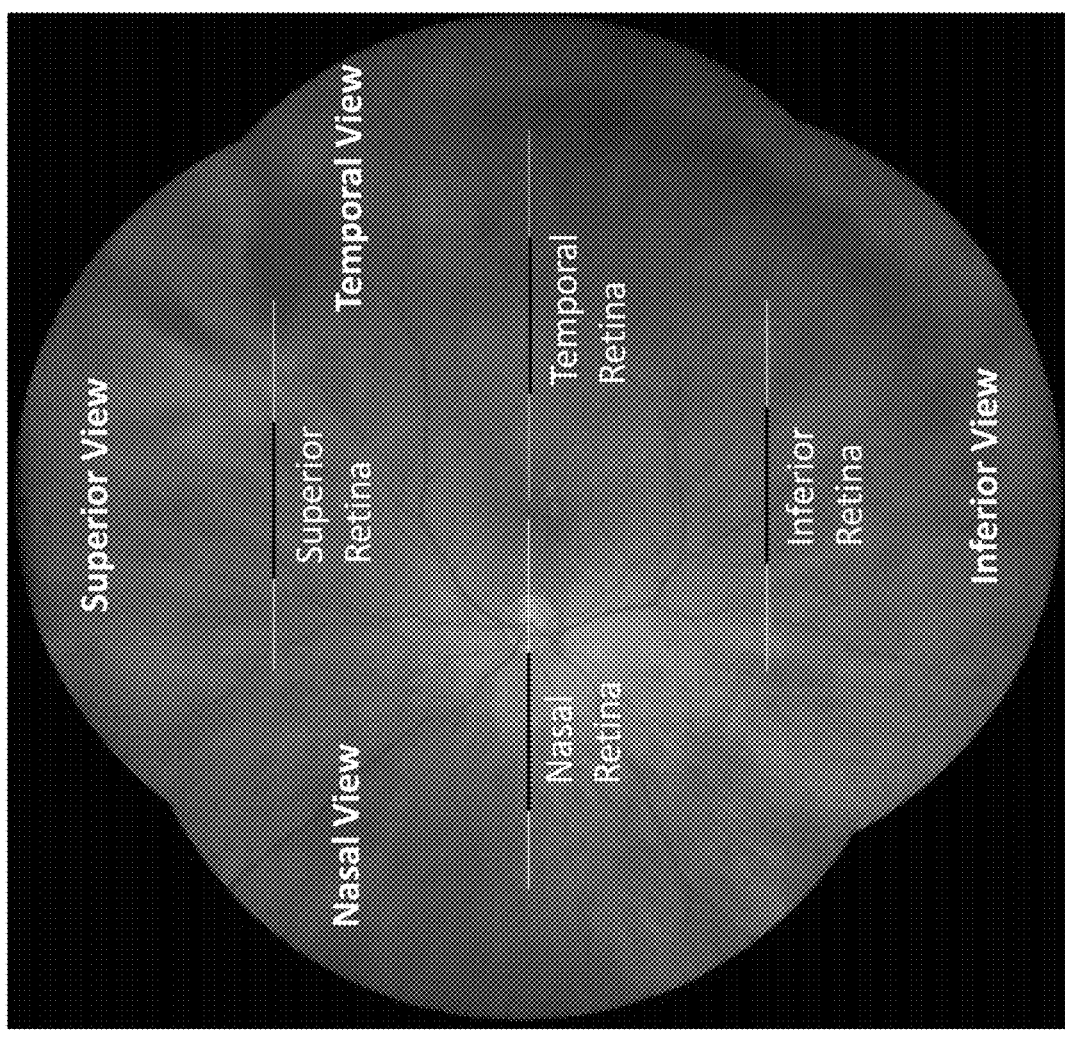
FIG. 2A illustrates an exemplary fundus camera view acquired with corresponding line scans from the spectrometer.
Figure 3B:
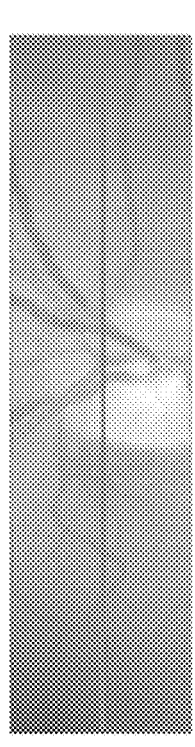
FIGS. 3B, 3C, and 3D illustrate exemplary images from a spectrometer, hyperspectral camera, and color fundus camera.
Figure 3B:
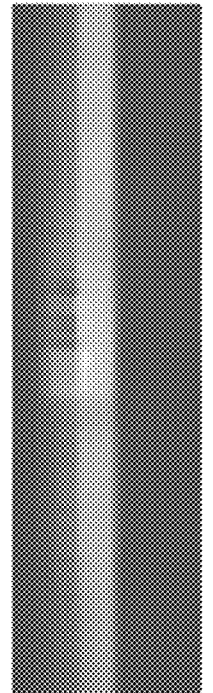
Figure 3A:
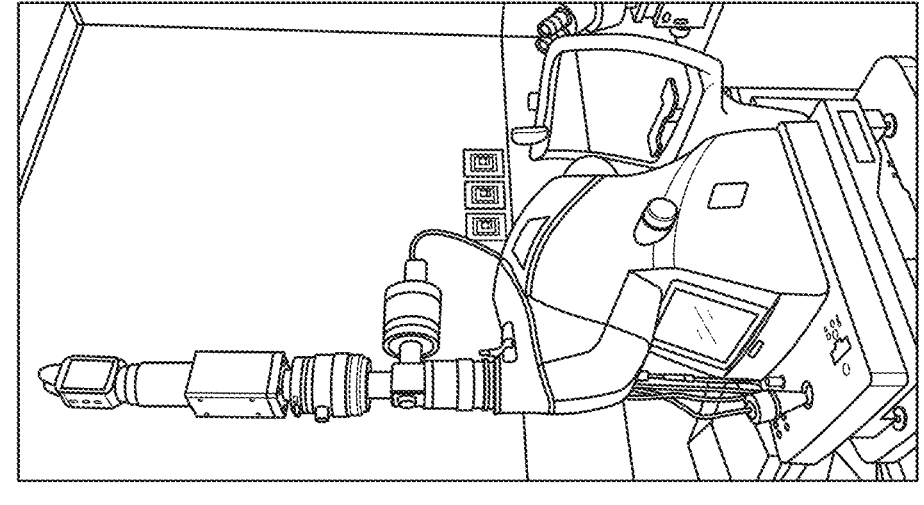
FIG. 3A illustrates an exemplary fundus camera.
Figure 3D:
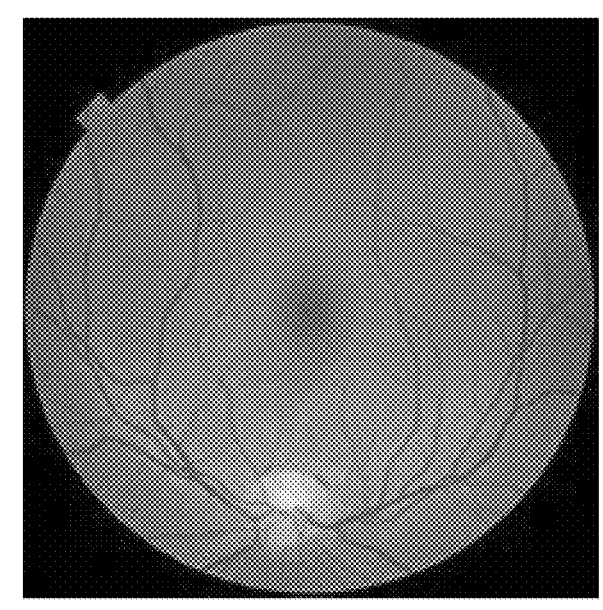
Figure 3C:
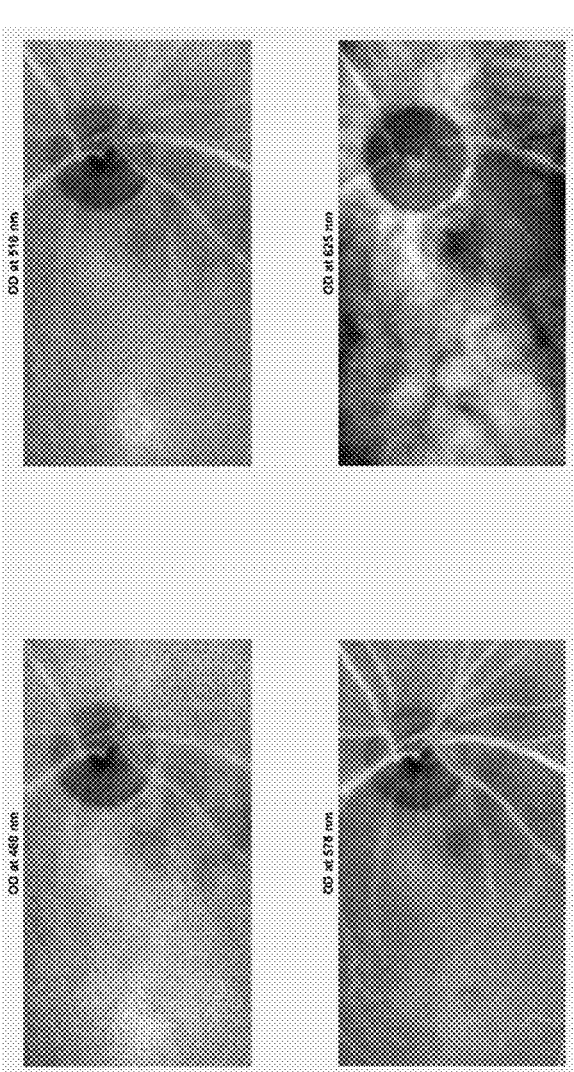

FIG. 1E is a more detailed schematic of an embodiment in which spatial spectra from the fundus of the eye can be acquired with a retinal viewing device 101 such as a fundus camera (i.e., Topcon NWB, EX, or DX) with an external camera port. Illumination is provided by a light source 103 which may be a xenon flash lamp integrated within the fundus camera, and the light is directed toward the eye by optical elements 104 which includes the fundus camera objective lens. Optical elements 104 also receives light reflected from the eye and direct it toward the eternal camera port. A field lens 107 is attached to the external camera port of the fundus camera. Light exiting the field lens is split by a beamsplitter 108 into two beam paths. The relative intensities of the beampaths from the beamsplitter can be 50/50, 30/70, or other combinations to optimize the signals collected by each imaging device. One beam path of the beamsplitter passes through a 60 mm focal length macro lens 110 and then to an imaging device 113 which may be optical spectrometer 111, such as a Specim VIR V10E or a Specim VNIR V10E, with a camera 112 such as a PCO pixelfly camera. The other beam path of the beamsplitter 108 passes through a 60 mm focal length macro lens 109 and is connected to an imaging device 102 such as a digital single lens reflex camera (i.e., Canon E90) or a snapshot hyperspectral imager (i.e., Ximea MQ022HG-IM-SM4X4-VIS). Outputs from imaging devices 102 and 113 are coupled to a computing device 106. A triggering mechanism 114 may be coupled to the imaging devices to synchronize their timing, and the triggering mechanism may be coupled to the computing device for control of the triggering signal. The triggering mechanism may further control the timing of a light source such as the flash of a xenon lamp, or in other embodiments the xenon flash lamp of a fundus camera may trigger the acquisition of images on the imaging devices such that they capture images of the eye when it is illuminated by the xenon flash. Using a fundus camera, various view of fundus can be acquired as shown in FIG. 2A. Fundus camera views that are acquired are shown in FIG. 2A with corresponding line scans from a spectrometer. FIG. 3A illustrates an exemplary fundus camera, and FIGS. 3B-3D illustrate exemplary images from a spectrometer, hyperspectral camera, and color fundus camera.

The light source may be a broadband light source, which emits a wide spectrum of light, for example, in the UV, visible, near infrared, and/or infrared wavelength ranges, or it may be a narrowband light source which emits a narrow spectrum or single wavelength of light. The light source may emit a single continuous spectrum of light or it may emit more than one discontinuous spectra. The light source may emit light with a constant wavelength range and intensity or the wavelengths and intensity may be adjustable. The light source may be comprised of a single light source or a combination of multiple light sources of the same or different types described above. The light source may be a xenon lamp, a mercury lamp, an LED, or any other light source. The light source may direct light toward the retina through the retinal viewing device, using the same optical assembly configured to collect light reflected from the retina, or it may direct light toward the retina through a different optical path.

In some embodiments, one or more optical filters may be used to filter the output of the light source or to filter the light reflected from the retina, or to filter light entering one or more imaging devices, so that only selected wavelengths of light are received by the one or more imaging devices. The optical filters may be adjustable or switchable (i.e. a filter wheel or an acoust-optic tunable filter) such that one or more wavelengths or wavelength ranges of light can be selected to pass through the filter at the same time or in sequence.

The imaging device may produce a spatial image, a spectral measurement, or a spatial-spectral image. A spatial image is a two-dimensional image with a single light intensity value for each image pixel, such as produced by a monochrome (grayscale) camera. A three-dimensional spatial image may also be produced using an imaging device such as optical coherence tomography (OCT), confocal microscopy, or others. A spectral measurement is a measurement of the wavelength components of light, such as produced by an optical spectrometer. A spectral measurement may be of a narrow or broad range of wavelengths and may be of a continuous or discontinuous set of wavelengths or wavelength ranges (spectral bands). A spectral measurement can be made based on absorbance, reflectance, wavelength shifts (such as Raman spectroscopy which measure a wavelength shift relative to a narrowband light source such as a laser), or other spectral properties. The imaging device can be one or more of a camera, a spectrometer, a hyperspectral device, multispectral device, an RGB camera, a microscope (regular or confocal), or optical coherence tomography system which contain imaging devices (like a camera) configured to receive an image and communicate with a computer to transmit the image for analysis. The imaging device can be in the form of a stand-alone device or a sensor to be incorporated into a retinal viewing device or a similar device.

A spatial-spectral image (or simply "spatial spectra" or a "spectral image") is a two-dimensional image with a spectral measurement of the light for each image pixel. For example, a spectral-spatial image can be seen as a 3D image where the third dimension is the spectrum. In some embodiments, a spatial-spectral image can include spatial information that can relate to an anatomical location. In some embodiments, a spatial-spectral image can include information related to patterns, formations and/or textures in the imaged region that can be seen based on the different wavelength at which the images are captured. For example, certain pathology formations may be observed at one or more, but not all wavelengths. A spatial-spectral image can be produced by a hyperspectral camera, a multispectral camera, or by scanning a point spectrometer in two dimensions or scanning a line spectrometer in one dimension (also known as a push-broom or whiskbroom imager). A line spectrometer can also produce a one-dimensional spatial-spectral image with a spectral measurement for each pixel along a line without scanning (i.e. lxn), and a point spectrometer can produce a point 'image' (i.e. 1×1) without scanning Some imaging techniques also allow the production of three-dimensional spectral images in which a spectral image is produced for each pixel in a three-dimensional volume. In general, a multispectral camera tends to produce images with higher spatial resolution but lower spectral resolution, such as in a color (RGB) camera (which measures three wavelength components, but other multispectral camera may measure 10 or more wavelength components or spectral bands) while a hyperspectral camera tends to produce images with higher spectral resolution but lower spatial resolution. A scanning spectrometer can produce images with both high spatial resolution and high spectral resolution but requires additional scanning optics and software. A spatial-spectral image can also be produced using a monochrome camera and sequentially measuring different wavelengths by illuminating the target with light of different wavelengths (by changing the light source and/or the wavelengths of light emitted from the light source, and/or by changing the optical filters used at the output of the light source) or by placing optical filters at any point in the optical path between the light source, the target, and the camera to filter the light received by the camera.

A purely spatial image can also be produced from a spatial-spectral image by combining the individual wavelength component measurements at each pixel into a single intensity value for that pixel, such that a hyperspectral camera can be used to produce both spatial-spectral and spatial images. In some embodiments, the light source and/or the imaging device may be contained within the same housing as the retinal viewing device, may be attached to the retinal viewing device, or may be separate from the retinal viewing device. For example, a fundus camera can be used to image the fundus of the eye by providing broadband illumination and imaging optics, including an integrated or external camera to capture the image of the fundus of the eye. In some embodiments, more than one imaging device can be used to capture images at the same time or in sequence. This can be done in order to obtain both images with high spatial resolution and images with high spectral resolution using different imaging devices. This can also be done so that the image from a first imaging device can be analyzed to identify spatial and/or spectral features and determine which second imaging device should be used and/or which locations or portions of the retina to image with a second imaging device. In some cases, instead of using a second imaging device the first imaging device could be used with different settings to capture a second image of the retina with different spatial and/or spectral features. In some embodiments, a first imaging device could be coupled with the retinal viewing device to produce a first image and then a second imaging device could be coupled with the retinal viewing device to produce a second image.

In some embodiments, a beamsplitter (such as a partially reflective mirror) could be coupled to the retinal viewing device and used to split the light (in any ratio of intensity) collected by the retinal viewing device between two or more imaging devices coupled to the beamsplitter at the same time. In some embodiments, a beam redirecting device (such as a moveable mirror) could be coupled to the retinal viewing device and used to redirect the light (in any ratio of time) collected by the retinal viewing device to two or more imaging devices in sequence. Two or more beamsplitters and/or beam redirectors could also be used in series to split and/or redirect the light between three or more imaging devices. In general, the system can be comprised of a fundus camera to provide illumination and image the posterior of the eye (using an internal integrated camera), a beamsplitter coupled to the fundus camera's external camera port, a hyperspectral or multispectral camera coupled to a first output of the beamsplitter to acquire spatial-spectral images, and a spectrometer coupled to a second output of the beamsplitter to acquire high resolution spectral measurements of a point or line across the posterior surface of the fundus.

In some embodiments, the outputs of the imaging devices can be coupled to a computing device, such as a computer (PC or laptop). In some embodiments, a spectral image can be read off a spatial-spectral imager to a computing device and wavelength calibration can be performed using a previously acquired spectrum of a mercury lamp, or other light source with well-defined spectral characteristics. The positions of wavelengths of the peaks in a mercury spectrum have well-defined characterized wavelengths via NIST standards. The known wavelengths and the position of the peaks in the mercury lamp spectrum can be compared with the spectrum measured by the spectral imaging device, and the pixels where those wavelengths and the position of those peaks appear in the measured spectrum, allowing for a pixel to wavelength mapping to be calculated for the image and the wavelengths of light in subsequent images to be known. The pixels in the spectral images where the peaks of the mercury lamp are measured can be assigned to the known wavelengths of those peaks. By noting the pixels where each of the known mercury lamp peaks is measured, an interpolation function can be calculated to map each spatial pixel to a wavelength value and this interpolation function can be used to correctly assign the wavelength values of each pixel in subsequent spectral measurements.

In some embodiments, registration can be performed between different spectral or spatial images to ensure alignment in space between images. This can be done be identifying corresponding spatial features in two or more images and shifting (translating and/or rotating) the positions of the images so that those spatial features overlap in a co-registered coordinate system. The calculated shift for each image to the co-registered coordinate system can then be used to shift subsequent images. In some embodiment when two or more imaging devices are used at the same time, triggering of the image capture can be performed to ensure alignment in time. This can be done by connecting a common triggering line to all of the imaging devices and delivering a triggering signal manually or from a computer to capture time synchronized images.

Figure 2B:
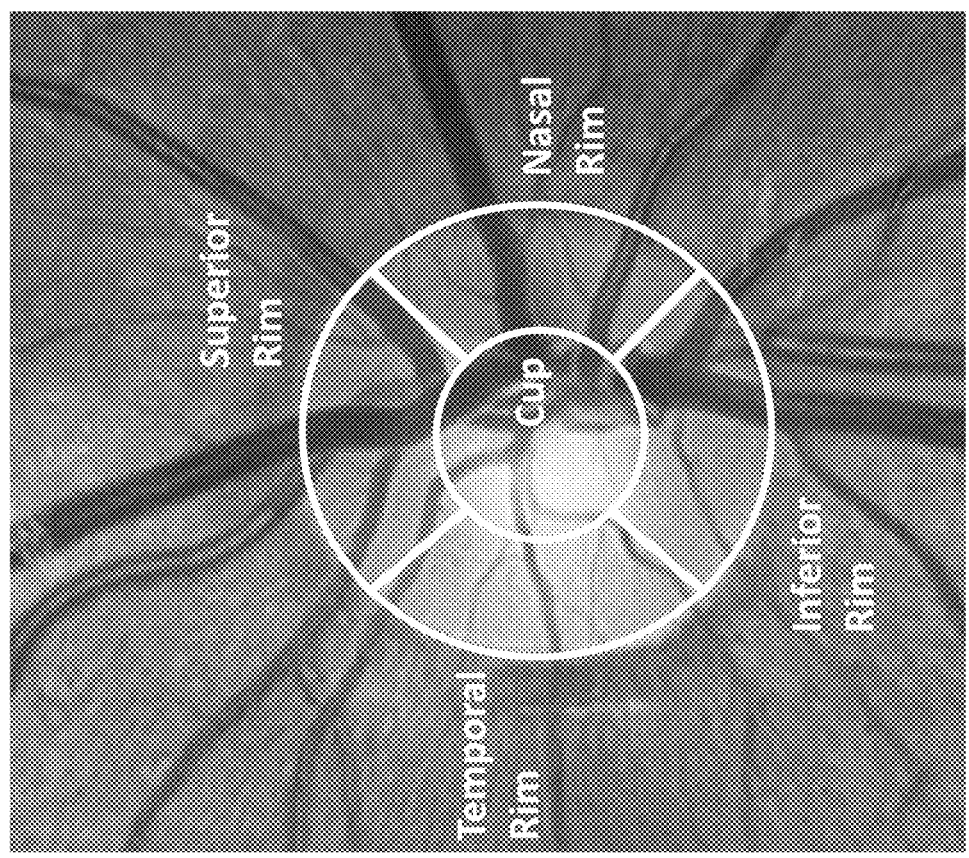
FIG. 2B shows the regions of the optic disc to be segmented.

The spectral image can be regionally segmented to identify pixels in the various components of the eye, including the optic disc (nerve head), retina, and fovea as shown in FIG. 2A. Furthermore, the regions within the optic disc can be further segmented into more specific components, including a temporal rim, nasal rim, inferior rim, superior rim, and cup regions as shown in FIG. 2B. The segmentation of the imaged components of the eye can be performed in a variety of ways. In some embodiments, the segmentation can be performed manually. In some embodiments, the segmentation can be performed by an automated segmentation algorithm. In some embodiments, the pixels in the temporal region of the optic disc are used in the subsequent calculations to determine a metric indicative of amyloid and tau status of the individual pixels. The values extracted from other regions can also contain information related to the amyloid or tau status of the individual as well as information related to other ocular or systemic pathologies. For example, the extracted values from other regions may contain amyloid or tau protein deposits measurable through spectral imaging or could exhibit the effects of these proteins on the tissues. Additionally, other regions may contain information related to other pathologies of the fundus, such as macular degeneration and diabetic retinopathy, which could also be measurable through spectral imaging.

Single Spectra Analysis

Figure 4:
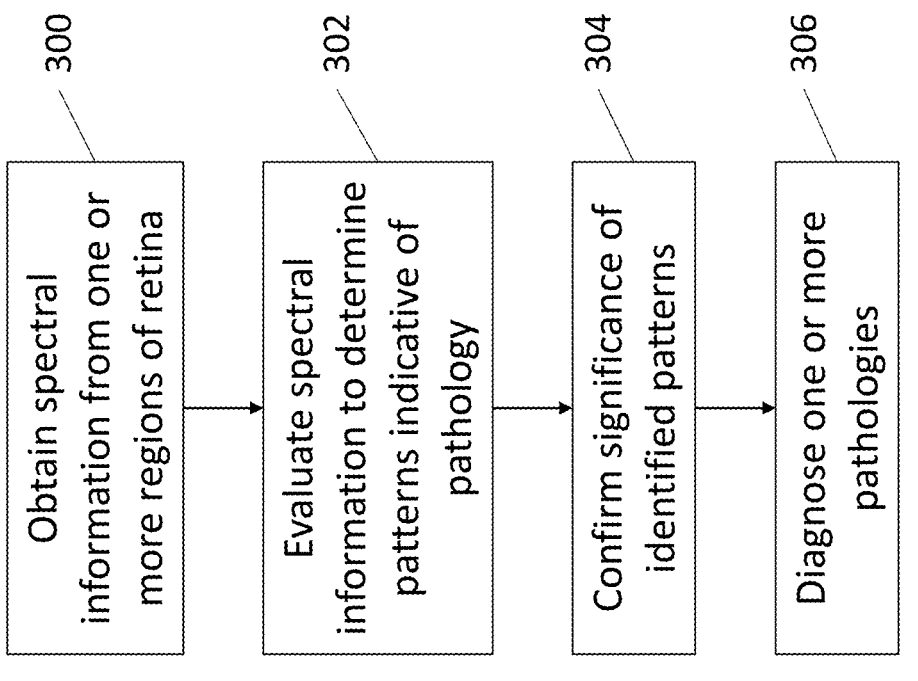
FIG. 4 is an exemplary flowchart of a method for processing a single spectral signal.

FIG. 4 illustrates an exemplary embodiment of a method for processing a single spectral signal. Spectral information is obtained from one or more regions of the retina in one or both eyes of a patient, in step 300. The spectral information associated with the images can be evaluated to determine one or more patterns indicative of pathology, in step 302. In step 304, a significance of the identified patterns is determined, and one or more pathologies can be diagnosed in step 306.

In some embodiments, the optical density and/or reflectance of the acquired spectra can be used to determine the presence or absence of the amyloid or tau formations. The method to determine the optical density and reflectance are covered below. In addition, the present disclosure provides a method for identifying wavelength range(s) of the optical density and reflectance, as well as optical density and reflectance ratios, that have significance with respect to the presence or absence of amyloid or tau formations.

Spectral values in the respective regions (disc regions, retina, fovea, etc.) are spatially averaged to produce an average spectrum for each region, $S_{ave}$, where $S_{ave}$ is the mean of all the pixel values contained in the region.

The average spectrum from each region is used in conjunction with a previously acquired white reference spectrum $S_{ref}$ to calculate the average optical density (OD). The white reference spectrum Sref is acquired by imaging a diffuse broadband reflectance standard target, for example a Spectralon target and calculating the mean spectrum of the acquired image. OD is a measure of how optically absorbing a material is, a higher OD value corresponds to a higher level of absorption by the material. The optical density of each region can be calculated as:

$$OD = \log(S_{ref}/S_{ave}).$$

The OD spectrum is normalized. This can be done by dividing the spectrum by a value between 700 to 800 nm, or by a value at some other wavelength, or through other signal normalization methods such as standard normal variate (SNV) normalization.

In some embodiments, the reflectance spectrum R can be calculated. The reflectance is a measure of the optical reflectance of the material being imaged, a higher value for reflectance indicates the material has higher optical reflecting properties. In some embodiments, the reflectance R can be calculated by:

$$R = \log(S_{ave}/S_{ref}).$$

In some embodiments, the reflectance spectrum is also normalized to a wavelength between 700 nm and 850 nm. Alternatively, reflectance spectrum can also be normalized via standard normal variate (SNV), minimum maximum, or other normalization methods.

Figures 5A, 5B:
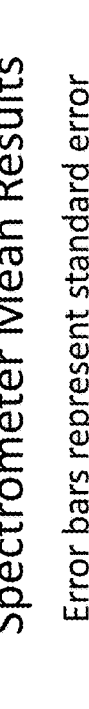
FIG. 5A illustrates an exemplary plot of an optical density spectra of disc of positive and negative amyloid status subjects.
FIG. 5B illustrates an exemplary plot of an optical density spectra of fovea of positive and negative amyloid status subjects.
Figure 5C:
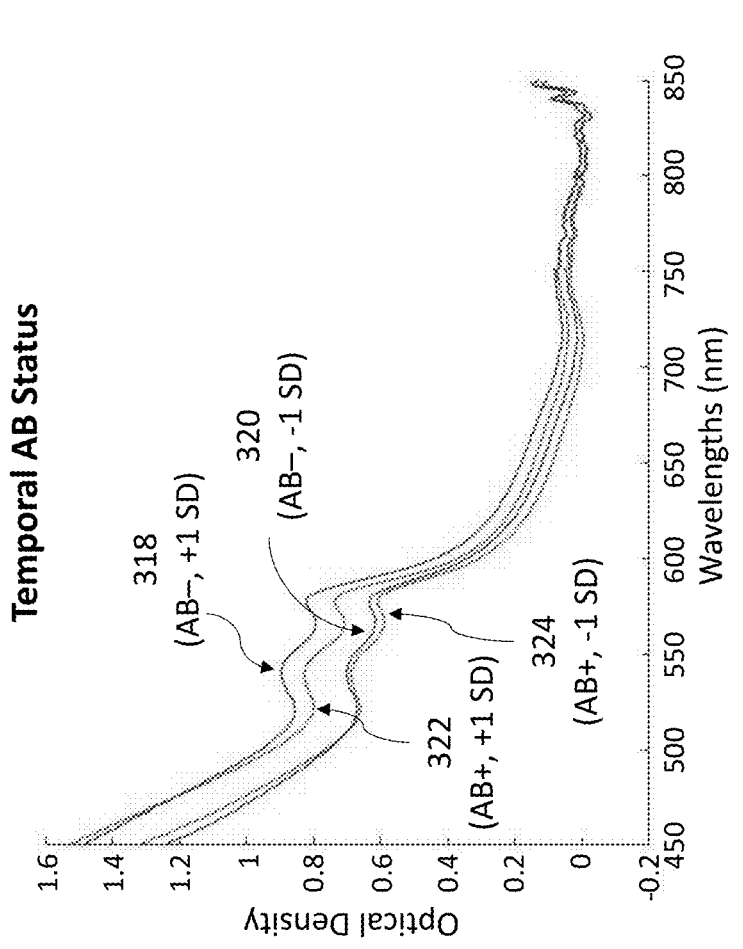
FIG. 5C illustrates an exemplary plot of mean results from the temporal disc region.

Example OD spectra are shown in FIGS. 5A, 5B, and 5C for total disc, fovea and temporal region of disc for subjects with positive and negative amyloid status. In FIG. 5A the optical density spectra of discs of subjects with negative amyloid status 310 are distinct from the optical density spectra of discs subjects with positive amyloid status 312. In FIG. 5B the optical density spectra of foveas of subjects with negative amyloid status 314 are distinct from the optical density spectra of foveas of subjects with positive amyloid status 316. In FIG. 5C the optical density spectra of the temporal disc region of subjects with negative amyloid status are shown bounded by one positive standard deviation 318 and one negative standard deviation 320 and are distinct from the optical density spectra of the temporal disc region of subjects with positive amyloid status as shown bounded by one positive standard deviation 322 and one negative standard deviation 324.

Figure 6:
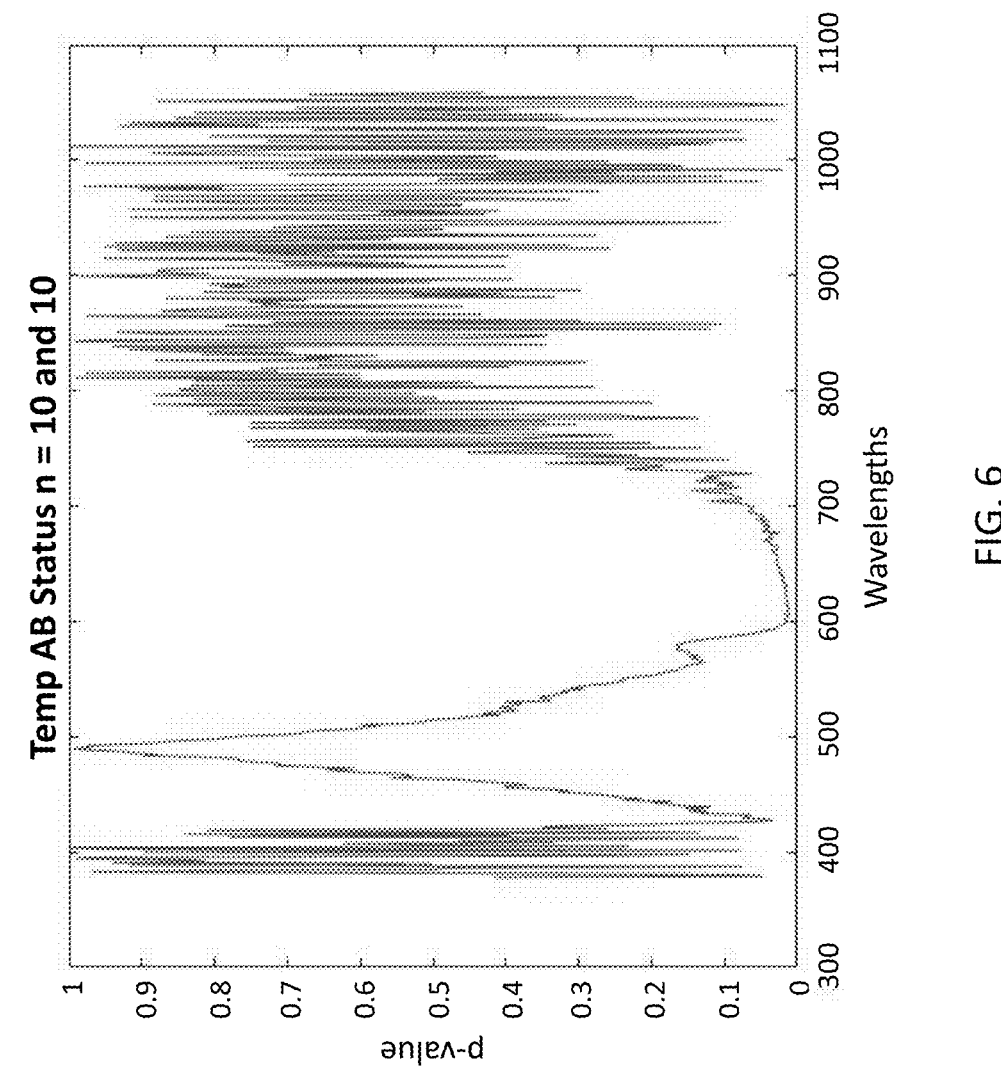
FIG. 6 illustrates an exemplary plot of wavelength significance of a reflectance signal in the temporal zone with amyloid status.

To assess which wavelengths or wavelength ranges the OD and R values correlate significantly with amyloid and tau status of a subject's status, a statistical significance test (e.g., students t-test) can be performed for the R and OD values at each wavelength for spectra acquired from a group of subjects having negative and positive amyloid and/or tau status. The statistical significance test identifies if the values at each wavelength are significantly correlated with the amyloid and/or tau status of the subjects. Examples of significance tests include t-tests, Pearson correlation, Spearman correlation, Chi-Square, ANOVA, among many others. Using the significance plots such as the one shown in FIG. 6, the wavelengths or wavelength ranges where the values are significant can be identified. In this example, significance is defined as having a p-value lower than 0.05, which is evident in wavelengths ranges 600-700 nm for the OD spectra. Once the wavelengths or wavelength ranges of significance have been determined, the system can be optimized (for cost, size, speed, and other factors) by selecting or designing imaging devices, light sources, and/or filters to only measure light at those wavelengths or wavelength ranges.

Such an approach can be used to evaluate the significance of spectral values for any status of the sample being measured and is not restricted to amyloid or tau status of a human. For example, it can be extended to other ocular pathologies and to measurements in other tissues, for example ocular pathologies include such pathologies as macular degeneration, diabetic retinopathy, and glaucoma, other tissues that could be measured include skin, muscle, tendon, blood vessels, and other tissues. In addition, the approach could be employed for tissues of other organisms. The approach would be the same for these different pathologies and/or tissue types but the spectral values determined to be significant may be different in each case. In some cases, it may be desirable to analyze samples for more than one pathology or disease state, for example to identify and diagnose subjects with more than one condition, or to identify subjects with a first disease state and exclude them from analysis of a second disease state if it is known that the presence of the first disease state would affect the results of the analysis for the second disease state.

Figures 7A, 7B:
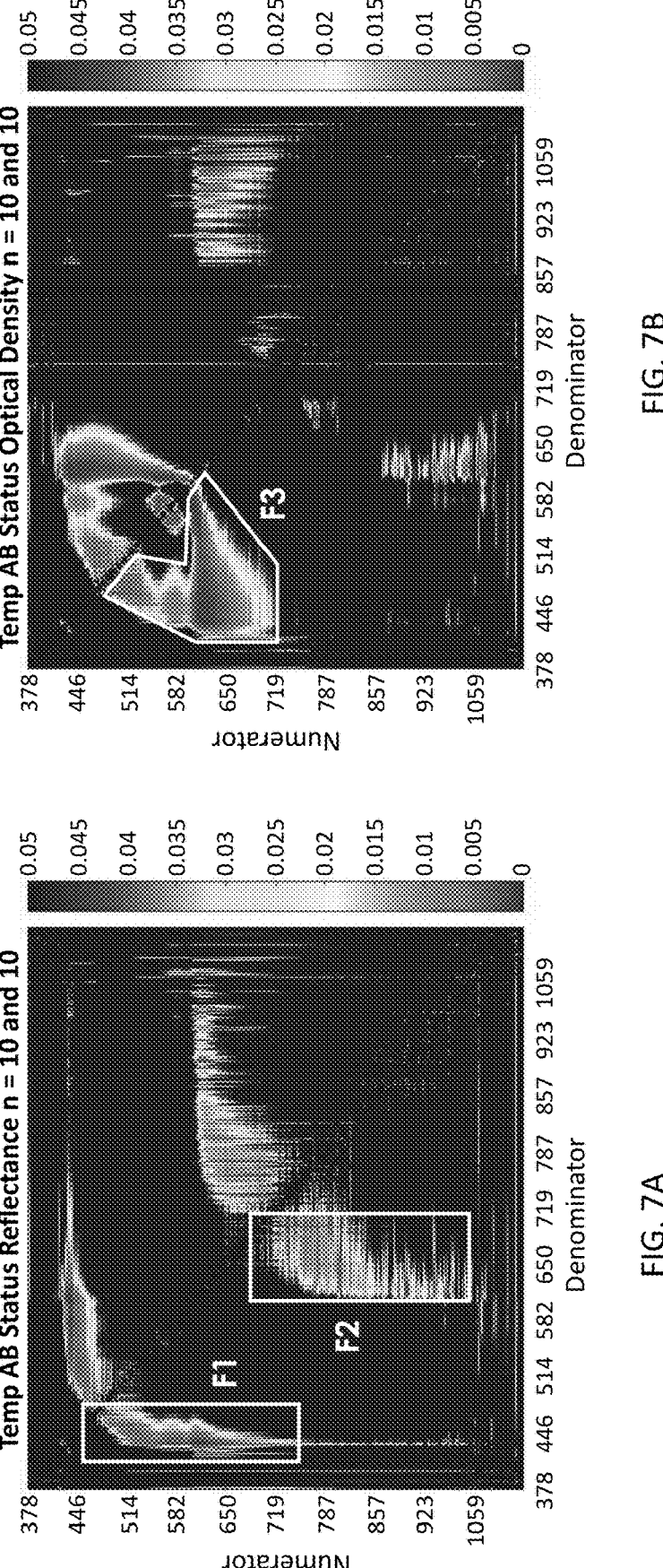
FIGS. 7A and 7B illustrate exemplary graphs showing wavelength significance of reflectance and optical density signal ratios in the temporal zone with amyloid status.

In addition to significance of R and OD values, the significance of ratios of R and OD values at various wavelengths can also be assessed. Each wavelength dependent spectral value of R and OD can be divided by all other R and OD values to assess all ratios for statistical significance. The results of these significance ratios can be plotted as a 2D image with the numerator and denominator of the wavelengths as the X and Y axis. Example 2D significance ratio plots are shown in FIGS. 7A-7B for an individual's amyloid status. In this example, significance is defined as having a p-value of less than 0.05, this evident in the outlined areas of each image. In the example shown in FIGS. 7A-7B, ratios regions identified (F1, F2, F3) show significance and are used as features for model development.

Figure 8:
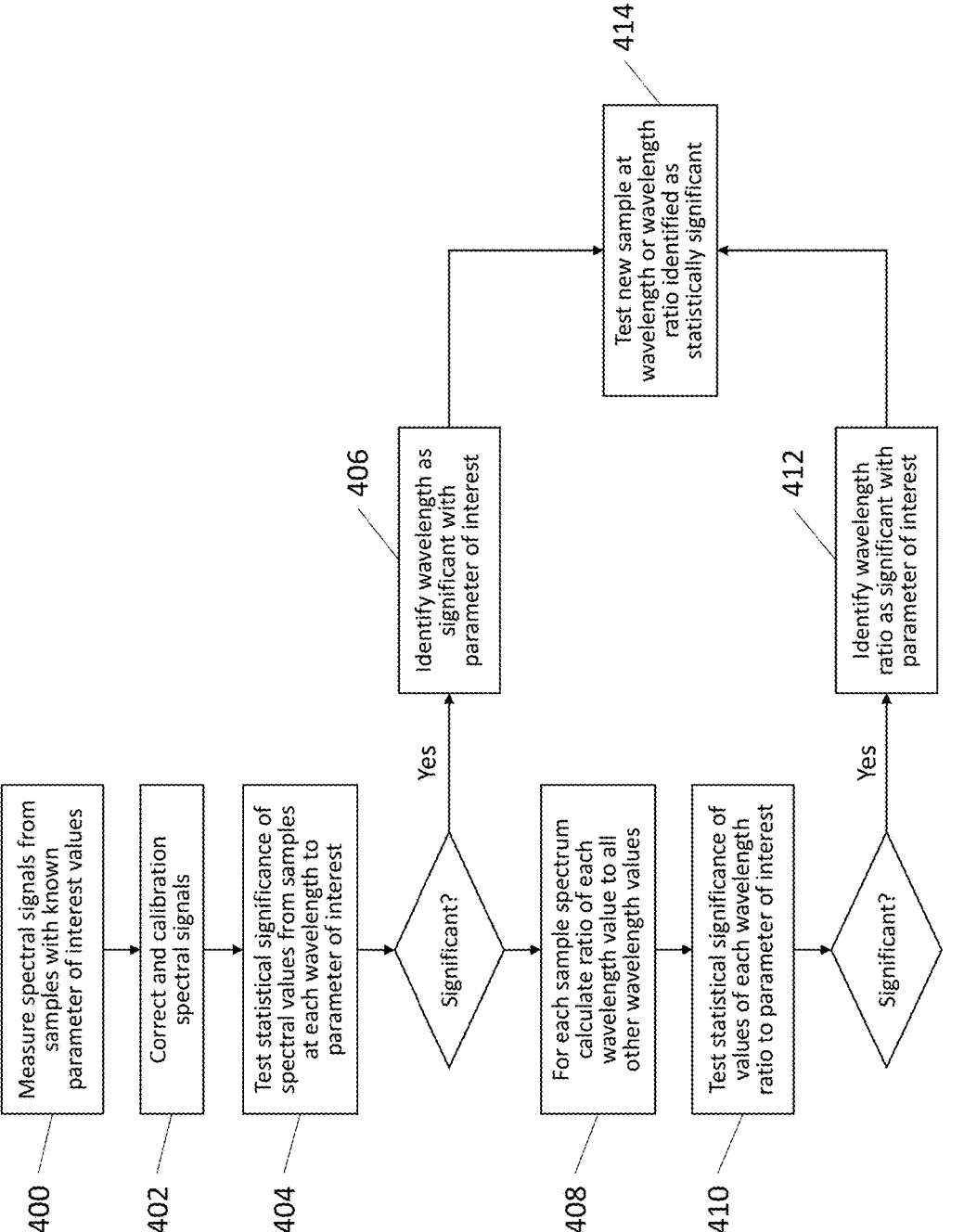
FIG. 8 is an exemplary flow chart of a method for wavelength feature identification

The general approach for assessing significance of values at each wavelength and the ratios of values at each wavelength is shown in FIG. 8. This process can be generalized to any spectral type of data to assess the signal for significance with a parameter of interest (in this case the amyloid and/or tau status of an individual. As shown in the exemplary flowchart in FIG. 8, a method for wavelength feature identification for values at each wavelength and for ratios of values at each wavelength can include the steps of measuring a spectral signal and correcting and/or calibrating the spectral signal (steps 400 and 402). The significance of spectral values at each wavelength to a parameter is calculated (step 404), and if that calculated value is found to be significant, that associated wavelength is noted as significant (step 406). If it is not found to be significant, a ratio of each wavelength to all the other wavelengths is calculated (step 408), and then the significance of spectral values at each wavelength ratio to a parameter is calculated (step 410). If that calculation is found to be significant, the wavelength ratio is noted as significant (step 412). Once a wavelength or wavelength ratio is found to be significant, a scan/image associated with the individual can be compared to a control image at the significant wavelength or wavelength ratio (step 414).

Such an approach can be used to evaluate the significance of the ratios of spectral values for any status of the sample being measured and is not restricted to amyloid or tau status of a human, for example it could be extended to other ocular pathologies. In addition, the approach could be employed for tissues of other organisms. The approach would be the same for these different pathologies and/or tissue types but the ratios of spectral values determined to be significant may be different in each case.

In some embodiments, the system may include spectral measurements in the mid-IR wavelength range, specifically in the range of 5900 nm-6207 nm and/or 6038 nm-6135 nm with specific interest at 6053 nm and 6105 nm wavelengths. The amyloid-β aggregation process can span many years and during this process the amyloid-β presents in both soluble and plaque form, folded into α-helix and β-sheet structures, with the relative concentrations of those structures changing over time. Those structures and their concentration ratio are a function of the progression of the aggregation process, which is an important biomarker to make clinical assessments of AD presence and progression. The different folding structures of this protein are known to have different spectral absorbance and reflectance, with the amyloid's α-helix structure having a peak at 6053 nm while the β-sheet of that protein has a peak at 6105 nm. The peak absorbance and reflectance observed in the retina is therefore an indication of the concentration ratio, for example a peak absorbance around 6079 nm would be evidence of a balanced mixture. The more that the ratio tends towards the peak absorbance of one of the structures, the greater the concentration of the structure having that peak absorbance. A spectral imager looking at the range of 6038 nm-6135 nm specifically can be used to measure these biomarkers. Other important wavelengths are 5900 nm, 6060 nm, 6150 nm, and 6207 nm which are related to structures that have clinical importance as well (such as β-hairpin, β-sheets, amyloid β1-42 fibrils, Tyr and Phe amino acid).

The methods disclosed herein of feature identification can also be extended to identify wavelength ranges of spectral values and wavelength ranges of spectral value ratios for the analysis of any sample of interest and is not limited to spectroscopy of the biological tissue. For example, this method can be extended for the use of pharmaceutical process monitoring, industrial process monitoring, hazardous material identification, explosive material identification, and food process monitoring. This approach can also be extended to other optical and spectroscopic modalities for the exploration of significant features with a property of interest in the sample. For example, this method can also be used with various optical modalities, including Raman spectroscopy, fluorescence spectroscopy, laser-induced breakdown spectroscopy, and other optical modalities.

The significant wavelength regions of both the R and OD spectra and the ratios of R and OD spectra can be identified as significant features of the spectra and used as inputs to a machine learning (ML) or artificial intelligence (AI) algorithm to predict amyloid or tau status of an individual based on a model trained on spectra acquired from individuals with a known status. The ML models can include methods such as logistic regression, decision tree, random forest, linear discriminant analysis, neural networks (including convolutional neural networks), naïve bayes classifier, nearest neighbor classifier or other ML or AI techniques.

Figure 9A:
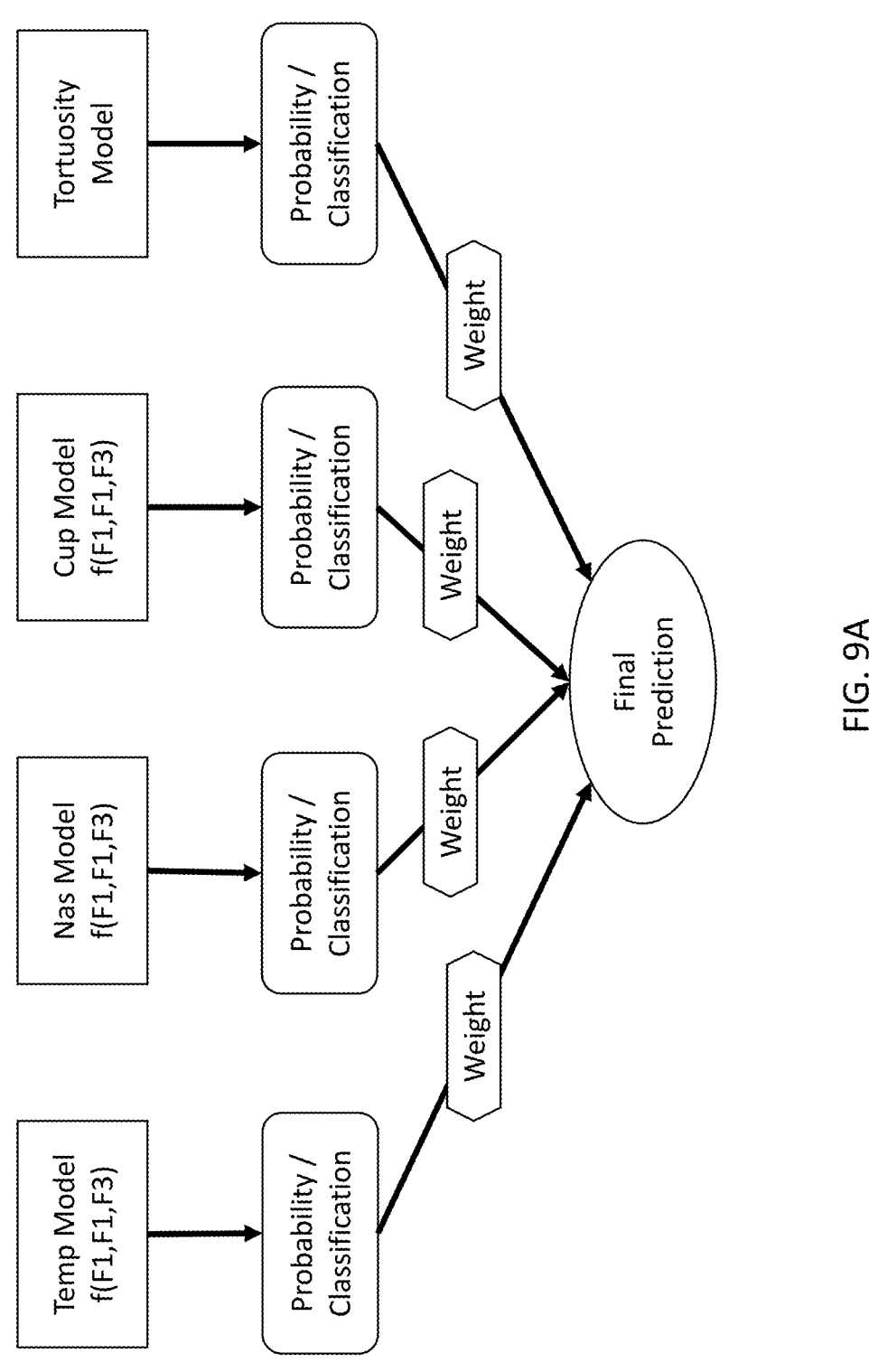
FIG. 9A shows an example of an ensemble prediction model employing various features from retinal imaging.
Figure 9B:
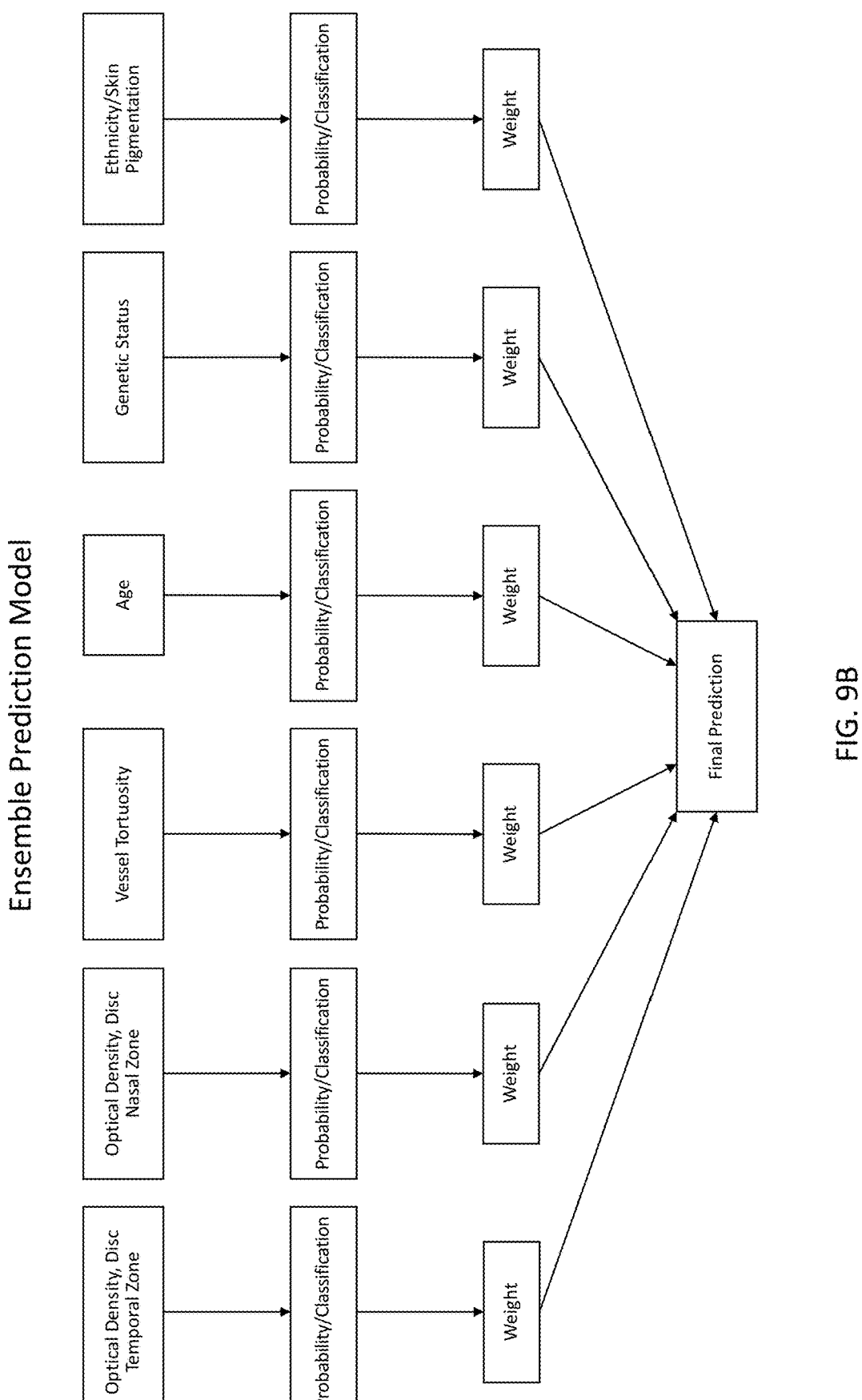
FIG. 9B shows an example of an ensemble prediction model employing various features from retinal imaging.

In some embodiments, an ensemble technique can also be employed as given in an example in FIG. 9A and FIG. 9B. Here the features identified by statistical significance testing previously described along with other features extracted from retinal imaging (such as blood vessel tortuosity) are used as features to train individual ML models, and the outputs of the models are considered in combination with various weights being applied to outputs of the models to calculate a combined output to predict the status of the individual.

The significant wavelength regions of both the R and OD spectra and the ratios of R and OD spectra are identified as significant features of the spectra and used as inputs to a machine learning (ML) or artificial intelligence (AI) algorithms to predict amyloid or tau status of an individual based on a model trained on spectra acquired from individuals with a known status. The ML models can include methods such as logistic regression, decision tree, random forest, linear discriminant analysis, neural networks (including convolutional neural networks), naïve bayes classifier, nearest neighbor classifier or other ML or AI techniques. Other ML approaches such as ensemble techniques can also be employed as shown in an example in FIGS. 9A-9B. Here the features identified by statistical significant testing previously described, along with other features extracted from retinal imaging (such as blood vessel tortuosity) are used features to train individual ML models, the outputs of these models are considered in combination with various weights being applied to outputs of the models to calculate a combined output to predict the status of the individual.

Such an ensemble model can include not only feature identified from hyperspectral, multispectral, and spectroscopic imaging, but also features extracted from retinal images including but not limited to tissue/vessel oxygenation, vessel tortuosity, cup-to-disc ratio, retinal nerve fiber layer thickness, and image texture metrics. In addition, demographic and other medical information on the individual could also be used as an input to such an ensemble model, including but not limited to age, sex, ocular pathologies, comorbidities, lens status (natural vs artificial), previous ocular surgeries, if dilation drops used during imaging, and any other demographics or health information.

In an ensemble model, the different data types (i.e. spectral, spatial, demographic, etc.) could each be processed by different machine learning or artificial intelligence algorithms independently, with the outputs of those algorithms then used as inputs to further algorithms, or multiple data types (i.e. combined spatial-spectral data) could be used by the same algorithm directly to produce an output based on an evaluation in multiple data domains. In some cases, the latter method is used since it is better able to capture correlations in data between multiple domains, and these correlations can be lost if the analysis to combine data types is performed only using the extracted outputs from independent algorithms rather than the full data sets.

In an ensemble model using spatial retinal images, the analysis algorithms may use the entire retinal image, portions of the retinal image, or only segmented sections of the image. This type of ensemble model can be used even if features such as the optic disc, which is often used as a reference for performing segmentation, are not present in the image. This type of model may analyze the entire image, such as in cases where the relevant information is unlocalized and appears over large areas of the image, or it may only analyze portions of the image or segmented sections of the image, such as in cases where the relevant information is highly localized.

In some embodiments, the machine learning or artificial intelligence algorithms can be designed to make pixel-wise predictions. Pixel-wise predictions are based on the spectral data for each pixel and the relationship between the spectral data from two or more adjacent or nearby pixels, rather than only data from a single pixel or the overall spectral data of a group of pixels together, as is the case in channel-wise prediction. Existing convolutional neural networks often use channel-wise pooling as the last layer or the network in order to create a feature vector. In these embodiments the channel-wise pooling is replaced with a pixel-wise pooling followed by maximum pooling. Pixel-wise predictions can be used because it prevents the algorithm from relying on multiple pieces of information that are spatially disconnected from each other, which is important when the relevant information is regional since a pixel-wise prediction reduces overfitting of the model and improves performance. Pixel-wise prediction also allow for a better ability to test, validate, and explain the algorithm outputs because unlike algorithms that rely on attention maps, input distortion, or other similar methods, this method allows verification that the location of the signal in the image corresponds to the correct area where the signal is expected to be, thus opening the "black-box" of the algorithm and making the output predictions more transparent.

Figure 10B:
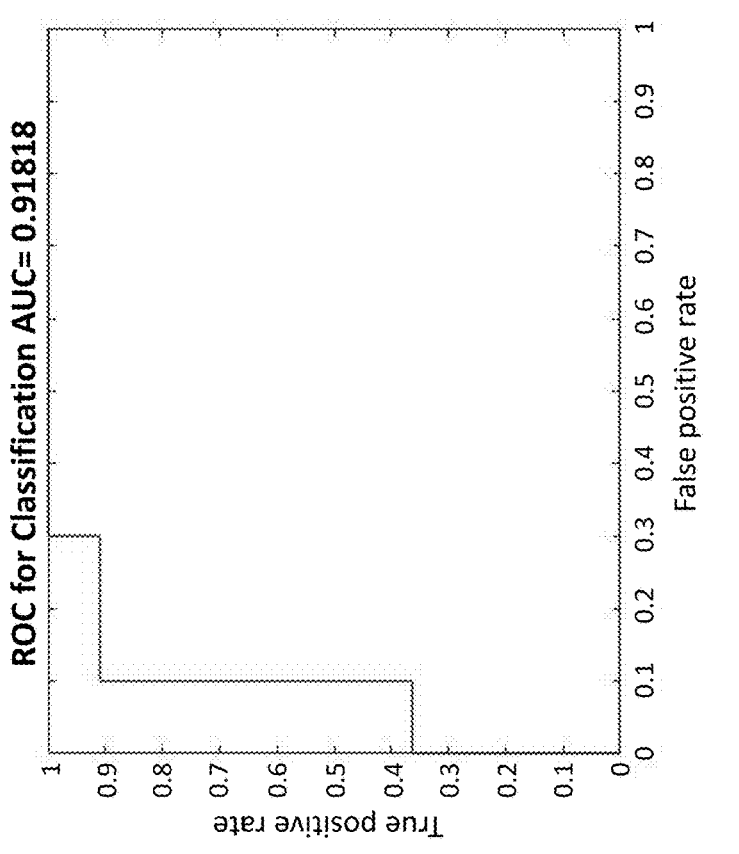
FIG. 10B illustrates an exemplary plot of the receiver operator curve for classification of amyloid status from the predictive model.
Figure 10A:
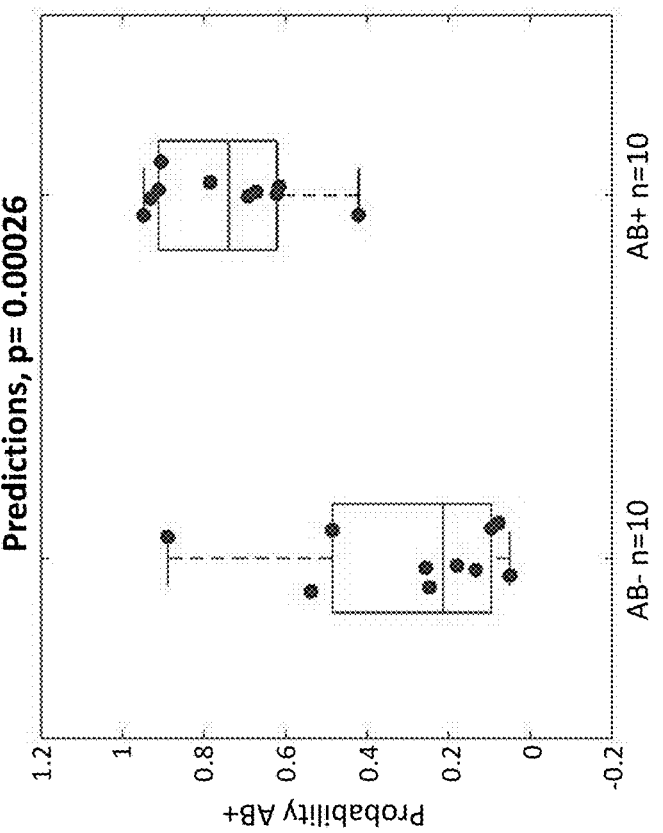
FIG. 10A illustrates an exemplary plot of the probability amyloid status as calculated from the ensemble model.

An example of the predictions of an individual's amyloid status based on an ensemble model using features from the R and OD ratio features from their eye is shown in FIG. 10A for 10 individuals with negative amyloid status and 10 individuals with positive amyloid status. The results of this model were evaluated through a receiver operator curve (ROC) in FIG. 10B providing an area under the curve (AUC) of greater than 0.9, indicating high predictive capabilities of the developed model for amyloid status.

Hyperspectral Analysis

Figure 11:
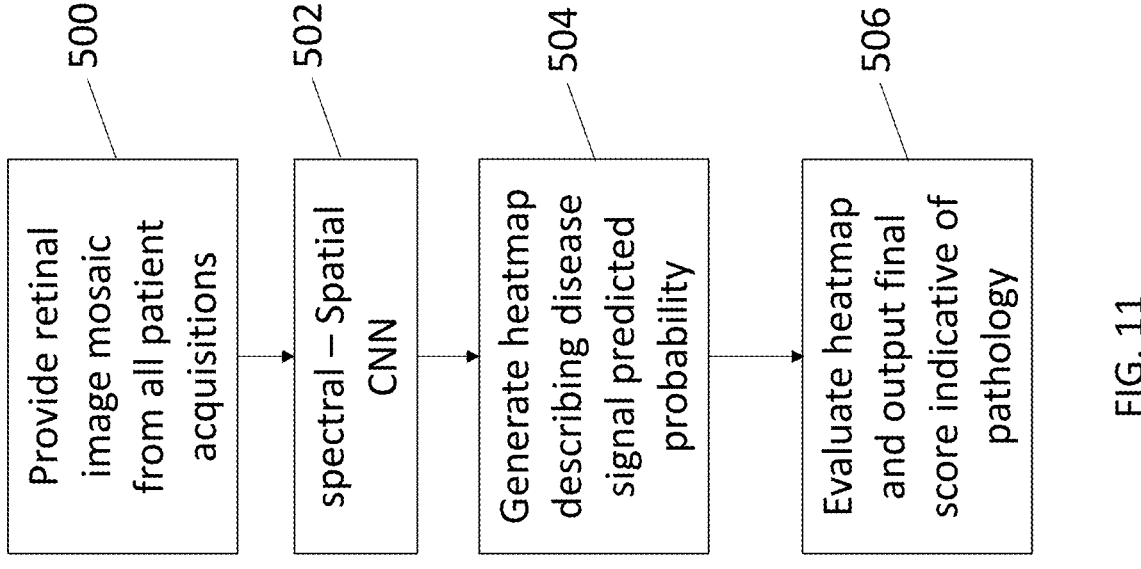
FIG. 11 illustrates an exemplary embodiment of a method for processing sets of hyperspectral or multispectral images.

FIG. 11 illustrates an exemplary embodiment of a method for processing sets of hyperspectral or multispectral images. A retinal image mosaic is provided from images acquired from a patient in step 500. A spectral-spatial CNN (step 502) is used to generate a heatmap describing disease signal predicted probability (step 504). The generated heatmap can be evaluated and a final score is output that can be indicative of pathology in step 506.

For a given patient, various sources of information may be available to assist with the prediction of amyloid or tau status. For example, patients may have spectral data from a subset of the regions, including the temporal, nasal, inferior, and superior rim of the optic disc, the cup, the fovea, along with various other spatial regions within the retina. Individual models can be developed using data from each of these regions. Additional models can also be developed using data from the tortuosity of vessels (as determined from the color or hyperspectral images), from nerve fiber thickness (as determined from OCT), from blood oxygenation, pupil dilation, inflammatory response, demographic data, etc. Each individual model will output the probability that a given subject has a positive or negative amyloid or tau status. Once all these models are trained, a prediction can be generated from an ensemble model, which combines all the models in which data is available for the given individual. The final prediction can be a weighted combination of the outputs from the available models. The weight given to each model can be based on how significantly the predictions from that model correlates with the amyloid or tau status of the subjects in the training set. These weights can be adjusted as additional data becomes available. The rationale behind the ensemble model is to deal with the reality each individual will have a different combination of data available to make the prediction (e.g., some subjects may have data from the temporal rim but not the inferior rim or vice versa). Additionally, different machine learning algorithms can be used to generate predictions for the various sources of data available. The choice of algorithms can be made based on the size and nature of the data.

In some embodiments, the design of the algorithm can build on top of state of the art algorithms from the convolutional neural network (CNN) family (such as EfficientNet, ResNeXt, ViT, Scaled-YOLOv4) and modifying the architectures to accept hyperspectral images instead of color (RGB) images, adapting the layers to support the spatial-spectral requirements of the analysis, and changing the width, depth and length of the networks according to the capacity needed for detecting signal in multispectral and/or hyperspectral spectral retinal images. Each model can be further adapted to replace the last layers (near the output) so that the last feature tensor of the network is pooled in a pixel-wise instead of channel-wise method.

The inputs to the neural network are a collection of HSI from both eyes for each patient. For example, for each eye up to 7 collection of images centered at different anatomical locations on the retina can be used. The locations can include one or more of the optic disk, the center of the retina, the fovea, superior, inferior, temporal, and nasal. In some embodiments, for each location line spectrograph data can optionally be acquired that crosses at the center of the image in a horizontal line. In some embodiments, for each eye a color Fundus image can be taken to possibly be used in AI to gain more insight and also for the ophthalmologist to determine diagnosis and pathologies such as retinopathy, macular degeneration, glaucoma, cataract, hypertension, etc.

Figure 12:
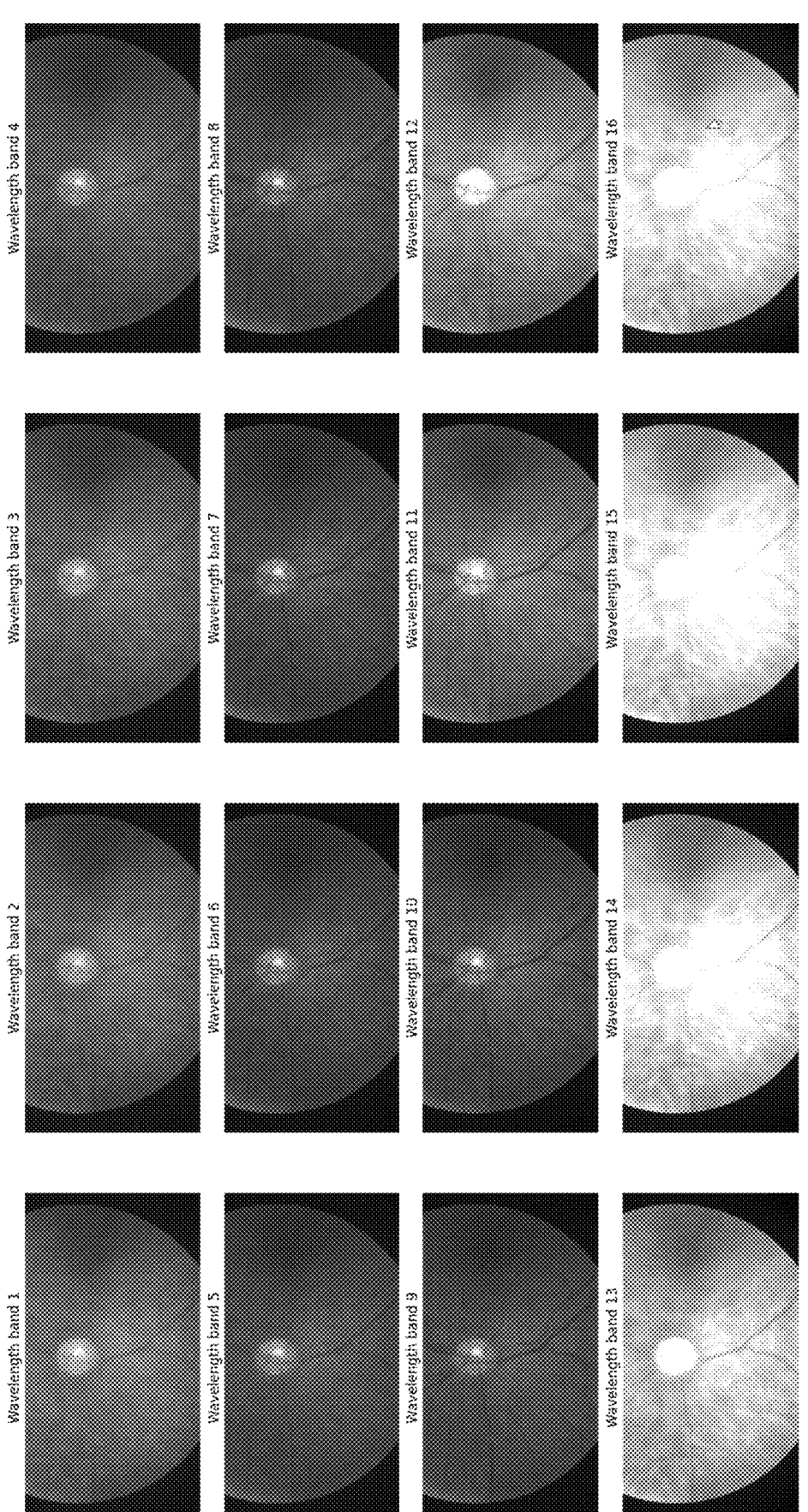
FIG. 12 illustrates an embodiment of a representation of multiple 3D images taken from a single location of a retina at multiple wavelengths.
Figure 13:
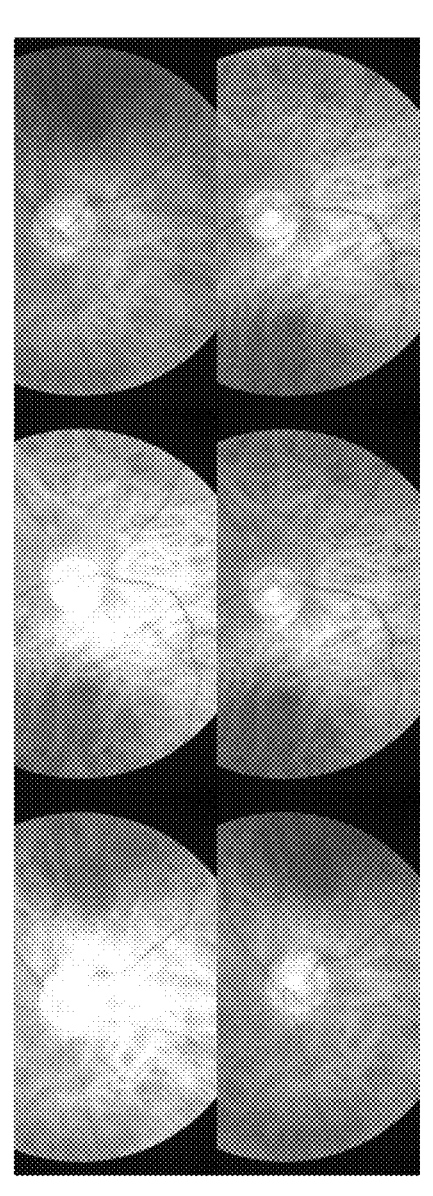
FIG. 13 illustrates stacks of images taken at 6 different locations on the retina that can be used as a CNN input.
Figure 14:
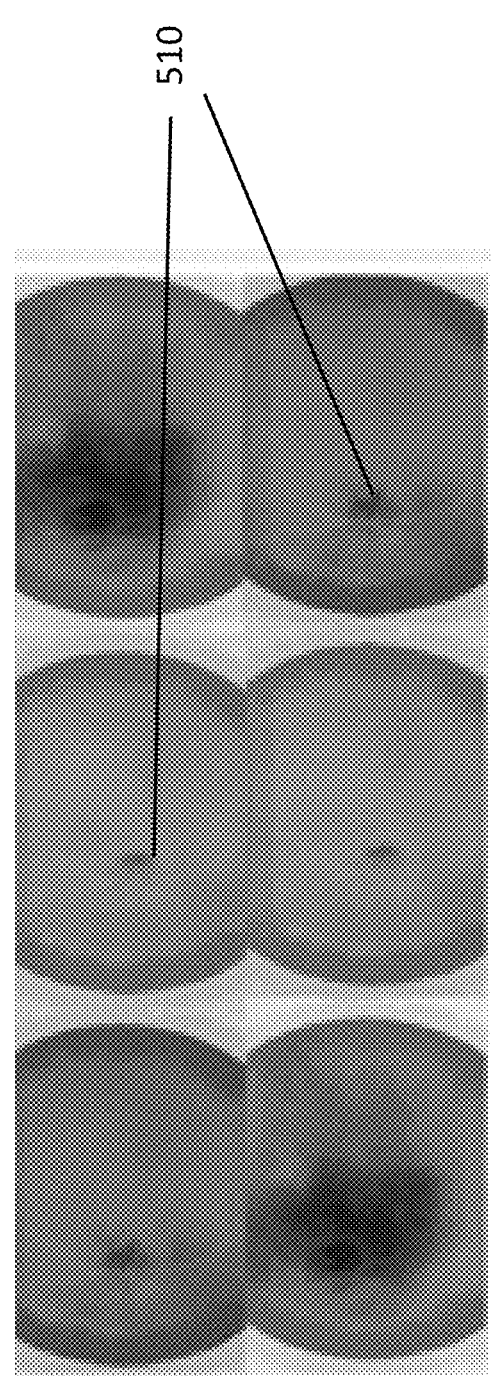
FIG. 14 illustrates an exemplary representation of images taken at 6 different locations of a heatmap overlaid on an image of the retina.

FIG. 12 illustrates an embodiment of a representation of multiple 3D images taken from a single location of a retina at multiple wavelengths. Images taken at different wavelength show different textures and structures. Each set of images from a single location becomes a stack of images that formed a portion of the images to the CNN. The input to a CNN can include a plurality of stacks of HSI taken at a plurality of locations of the retina. As shown in FIG. 12, different channels can show different textures and structures of the images. As shown, there are some vessels and other structures or textures that can be seen, for example, wavelength band 2, that cannot be seen in wavelength band 10, and vice versa. For example, FIG. 13 illustrates stacks of images taken at 6 different locations on the retina that can be used as a CNN input. The output from the CNN can include a probability score related to the likelihood of the existence of disease, and in some embodiments can include images such as the images shown in FIG. 14. FIG. 14 illustrates an exemplary set of images of the generated heatmap overlaid on the images shown in FIG. 13. In the background, there is a representation of the original retinal image, and the heatmap is a color overlaid on the background. The heat map shows one or more hot spots 510, which are spatial-spectral patterns indicative of protein formations. The overlay allows for a user to know where the hot stop falls in the original retinal image. These heatmap images can be used as an input into the AI.

In some embodiments, the algorithm can be trained using a database of corresponding data from patients with known disease state. A plurality of patients and a control set of health individuals can be used. Data can be acquired from each patient, and the data and/or images collected can be pre-processed. Low quality images (according to several criteria we defined in the patent already) can be excluded and the images can be normalized. The data can be split into three sets for training, validation and testing), using multiple folds in a cross-validation methodology and ensemble different models from different folds together using the training data before testing on the test set. In some embodiments, the training set is exposed to AI during training and is used for the actual learning, the testing set is frequently used during the train process to evaluate the performance of the model on unseen data, and the validation set can be held out, completely separate to the developers of the AI and is only used one time to validate the model on new data. Sometimes training can be difficult on a per-image level because the relevant information isn't apparent or doesn't exist in all of the images acquired from a single subject, for example if the information is apparent in an image of the optic-disc but not an image for the fovea, or if it is apparent in the left eye but not in the right eye. In such cases, training becomes difficult on a per image level as some labels (positive vs. negative) can be misleading to the AI. To address this problem, in some embodiments, some or all of the images of a single subject are concatenated into one mosaic of images and analyzed as one whole sample. In that way, even if the signal is apparent in only one of the images, the training labels assigned to this mosaic would be correct and not mislead the AI. In some embodiments, the final algorithm may be an ensemble of multiple algorithms, which is a common practice for ML/AI. Images are captured from a patient, poor quality images are excluded and recaptured, and the images are compiled into the same mosaic form as in the training data set before being used by the algorithm to produce a final score. When using the AI for prediction, some patients can be excluded based on certain clinical criteria. For example, if a certain pathology such as glaucoma or certain ethnicity were underrepresented in the training and validation sets, there can be less certainty that the AI will perform on them as required. The AI can be run on all the images and clinical data can be acquired from the patient.

Prior to using any of the collected or calculated spatial or spectral data, quality assurance criteria can be applied to ensure that the data is of sufficient quality to produce a reliable prediction output from the machine learning or artificial intelligence algorithm. For example, the spectral dynamic range, which is defined as the difference between the highest spectral band and the lowest spectral band in a specific pixel, can be calculated for each pixel in the hyperspectral or multispectral or spectrometer data, and pixels with a spectral dynamic range below a preset percentile threshold can be rejected, since data with low spectral dynamic range contains less information and may not be usable. As another example, a saturation ratio, defined as the number of saturated data points (i.e. at the maximum value of the measurement device) divided by the total number of data points of an input image, can be calculated and images with a saturation above a preset threshold can be rejected, since too much saturation results in a loss of information. A data point could be the overall intensity value measured at a pixel of the image, or it could be the intensity of only one or more spectral (wavelength) components at that pixel. However, not all saturation degrades the prediction power of the algorithms, and some saturation below the preset threshold can even, in some cases, improve it to some degree. This is because saturation in a small number of data points indicates that the signal being measured is reaching the maximum range of the imaging device, which indicates that the subject being imaged is illuminated and reflecting strongly such that the non-saturated data points are likely generating signals with good intensity and dynamic range that can provide a clear image and an accurate result. If no data points are saturated, then the subject may be under-illuminated and the full dynamic range of the imaging device is not being utilized. As a further example of a quality assurance criteria, the blurriness or sharpness of an image can be calculated based on changes in intensity between adjacent image pixels, and images or portions of images with blurriness above a preset threshold can be rejected, or the homogeneity of an image can be calculated based on changes in intensity across all image pixels, and images or portions of images with too much or too little homogeneity can be rejected.

For each of the 'quality assurance' criteria, there can be threshold values set at which data would be accepted or rejected. While the spectral dynamic range percentile can vary, in some embodiments the range is 20% spectral dynamic range for the $5^{th}$ percentile of pixels. In some embodiments, up to 5% saturated pixels can be allowed. Blurriness can be measured with a score from 0 to 1, with a 1 being completely blurry. In some embodiments, up to 0.2 blurriness measurement can be allowed. Homogeneity can be measured by looking at histograms in sub-sections of the image and calculating the entropy over the different histograms. In some embodiments, the threshold is set to reject images with entropy over 1.3. Based on the quality assurance criteria, the settings of the light source and/or imaging devices can be adjusted, for example by increasing or decreasing the intensity of the light source to improve the saturation ratio, and the procedure can be repeated.

In individuals with Alzheimer's disease, both the amyloid and tau levels in the brain are elevated prior to the onset of symptoms. The levels of amyloid and tau are correlated in that subjects who develop AD tend to have biomarker evidence of elevated amyloid deposition biomarkers (which is detected via abnormal amyloid PET scan or low CSF Ab42 or Ab42/Ab40 ratio) as the first identifiable evidence of abnormality, followed by biomarker evidence of pathologic tau (which is detected via CSF phosphorylated tau, and Tau PET). This may be due to amyloid pathology inducing changes in soluble tau release, leading to tau aggregation later. Because of this, the predictive abilities of these methods for prediction of amyloid status shown in FIG. 8 and the developed model for amyloid status can also be considered valid for predicting the tau status of an individual as the tau and amyloid levels are correlated.

Figure 15B:
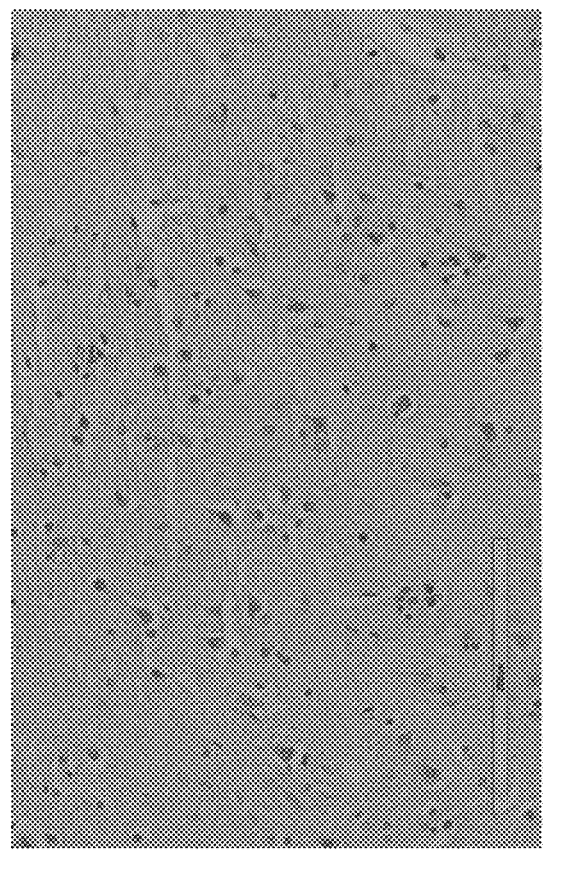
FIG. 15B shows the absence of amyloid and/or tau protein in a representative histology slide from a healthy subject.
Figure 15A:
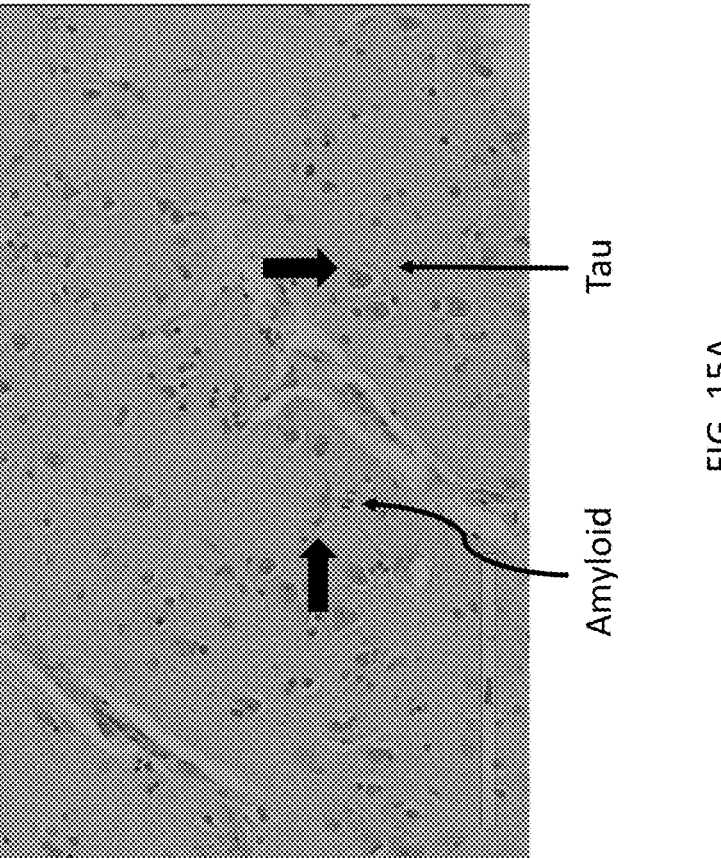
FIG. 15A shows the amyloid and tau proteins identified in a representative histology slide from a subject with Alzheimer's disease.
Figure 16:
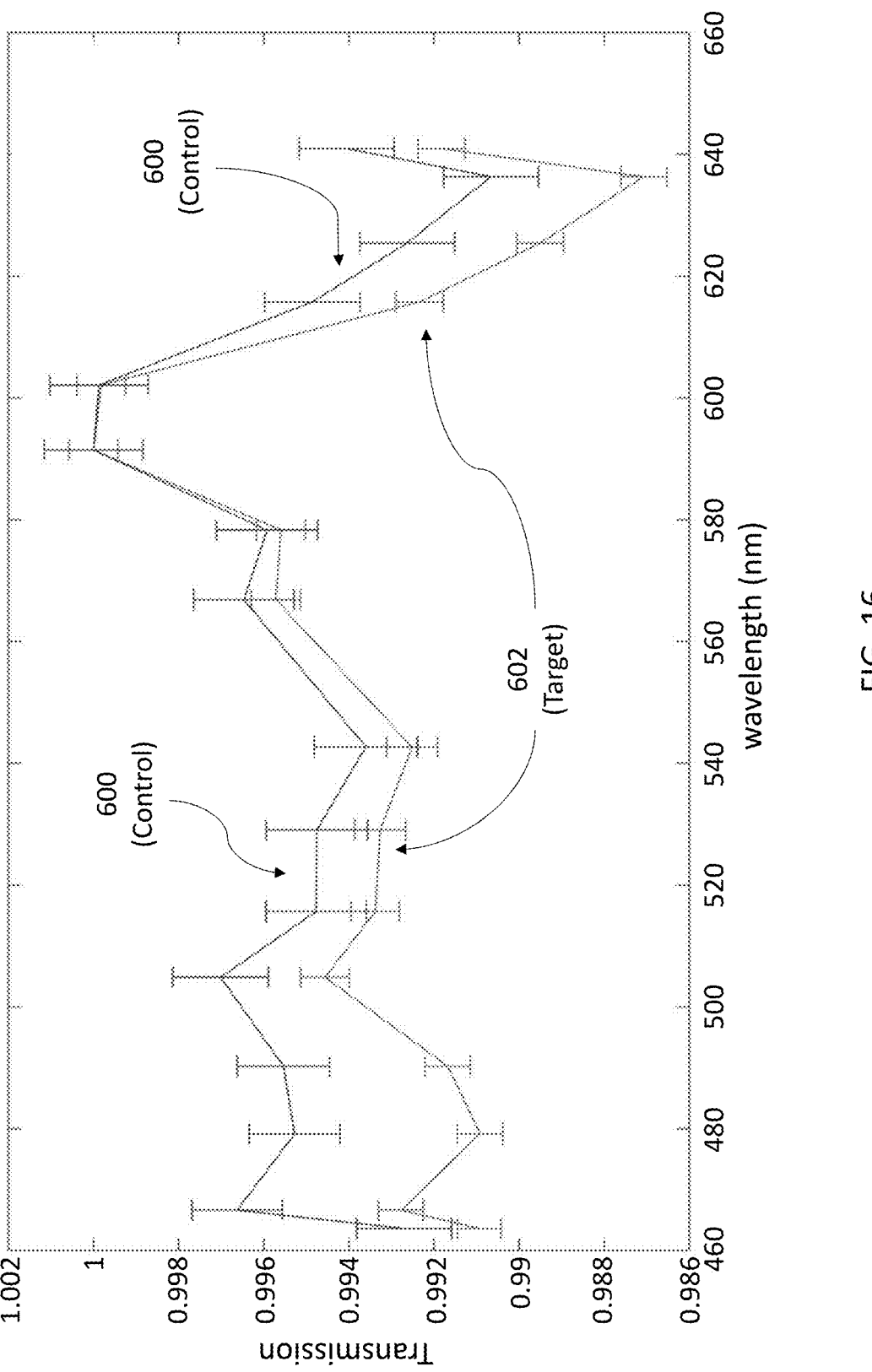
FIG. 16 shows the spectral transmission results through brain sections from the same subjects as those in FIGS. 15A and 15B.

The capabilities of hyperspectral imaging for detection of tau protein in tissue are demonstrated in FIGS. 15A, 15B, and 16. FIG. 15A shows an example histological slide of brain tissue from an individual with Alzheimer's disease stained with Congo red, having deposits of amyloid and tau protein that are identified throughout the tissue consistent with a diagnosis of Alzheimer's disease. FIG. 15B shows an example histological slide of brain tissue from a healthy individual also stained with Congo red, with no deposits of amyloid or tau proteins identified in the tissue consistent with a negative diagnosis of Alzheimer's disease. FIG. 16 shows corresponding hyperspectral measurements on brain sections from the same individuals histologically examined in FIG. 15A with amyloid and tau deposits compared to healthy control sample in FIG. 15B not exhibiting amyloid and tau deposits. Differences in the spectrum measured in tissues with and without tau protein are evident in FIG. 16, in particular a decrease in light transmission was measured through the tissue sections from individuals with tau deposits, this reduction in light transmission is theorized to be due to the absorption of these wavelengths of light by tau proteins. A target line 602 is the mean of those with Alzheimer's disease and a control line 600 is the mean of health individuals. The reduced transmission in those with tau and amyloid protein (i.e., those with Alzheimer's disease) demonstrates the ability to differentiate health tissue from that with tau and amyloid protein. These results indicate that spectral measurements can be used to discriminate healthy tissue from tissue containing tau protein.

As the eye is an extension of the central nervous system, linked by the optic nerve directly to the brain, proteins produced in the brain as part of Alzheimer's disease progression such as beta amyloid and tau migrate from the brain to the fundus of the eye. As such, the detection of these proteins in the eye can be indicative of the presence or absence of these proteins in the brain and corresponding risk of developing Alzheimer's disease. The ability to measure tau in brain tissue as shown here further demonstrates the feasibility to also measure tau in ocular tissues, such the retina and optic disc, and use these measures as a proxy for the levels of tau in the brain.

In some embodiments, the methods described herein can be used to analyze the vessels and vessel walls of the retina, as shown in FIGS. 17A-17B. An algorithm can be used to extract an accurate vessel segmentation from the captured images, and the AI can be used to pinpoint markers for amyloid along the vessels, i.e., vascular amyloidosis. It extends to lots of vascular changes, and other vascular pathologies that can be relevant to ocular diseases and amyloid related diseases, such as cerebral amyloid angiopathy (CAA). As shown in FIG. 17B, a model can be used to segment the vessels (step 700), and a projection can be developed (step 702). Vessel segmentation can be extracted (step 704), and the AI can be used to identify amyloid markers along the vessels (step 706).

Figure 17C:
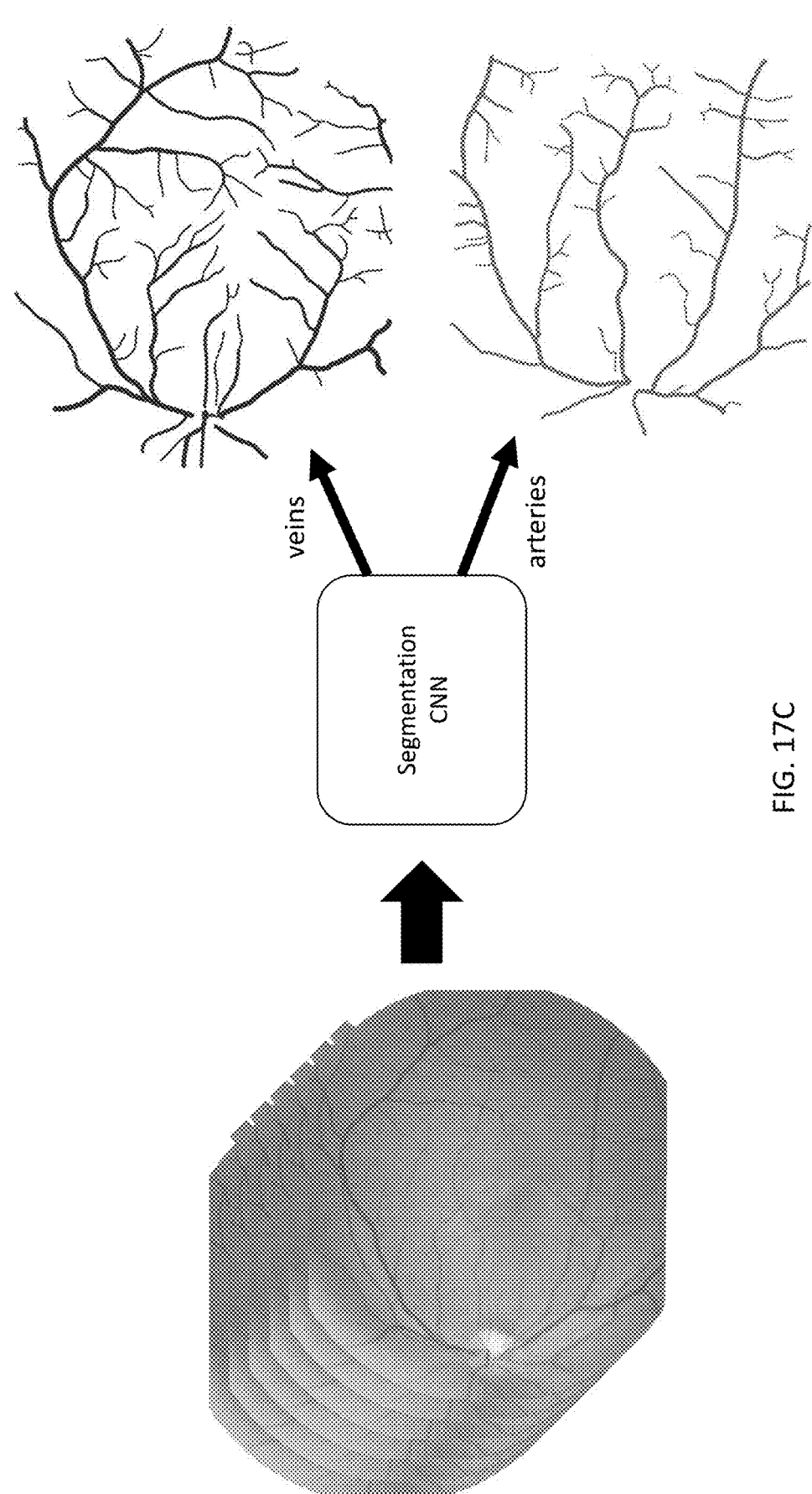
FIG. 17C illustrates an exemplary representation of segmentation of blood vessels in a retina using an AI.

A CNN segmentation AI is developed to automatically extract vessels from images, such as HSI images. The HSI images are input into the AI and it outputs two probability maps indicating the segmentation of the vessels, as shown in FIG. 17C. One map for arteries and the other for veins. Those maps are themselves images where the brightness of each pixel is higher where the AI predicts the existence of a vessel. These maps are binarized by a threshold, usually equals to 0.5 but can be configured. The output binary segmentations of arteries and vessels are fed to another AI that processes the structure of the vessels as well as the spectral signature along the vessels to detect the biomarkers related to the disease.

In some aspects, the present disclosure provides a system for measuring optical properties of an eye that comprises a retinal viewing device; a light source configured to illuminate the retina of the eye being viewed by the retinal viewing device; one or more imaging devices configured to receive light reflected by the retina from the light source and produce one or more spatial or spectral images of the retina; and a computing device configured to receive the images produced by the one or more imaging devices, calculate one or more metrics indicative of disease state based on the images, and make a determination of disease state. In some embodiments, such determination can be made using a machine learning or artificial intelligence algorithm to compare one or more of the metrics indicative of disease state with a database of corresponding values measured from subjects with known positive and negative disease state.

In some embodiments, the one or more imaging devices comprise at least one hyperspectral or multispectral imager and at least one optical spectrometer. In some embodiments, at least one spatial image and at least one spectral image are produced by the same imaging device or generated by the computing device from the output of the same imaging device. In some embodiments, the system further comprises one or more optical elements that allow two or more imaging devices to receive light reflected by the retina and produce images of the retina at the same time or in sequence. In some embodiments, the system further comprises one or more optical filters to limit the wavelengths of light emitted by the light source or received by one of more of the imaging devices. In some embodiments, one or more metrics indicative of disease state are calculated based on discontinuous wavelengths or wavelength ranges in the spectral images. In some embodiments, the discontinuous wavelengths or wavelength ranges are selected by determining the wavelengths relevant to one or more metrics indicative of disease state using a machine learning or artificial intelligence algorithm to compare a database of spectral images measured from subjects with known positive and negative disease state.

In some embodiments, the light source is configured to emit light only at wavelengths relevant for calculating the metrics indicative of disease state, or where the system further comprises optical filters to limit the wavelengths of light received by one or more imaging devices to the wavelengths relevant for calculating the metrics indicative of disease state. In some embodiments, the system further comprises a trigger control to synchronize one or more of the imaging devices or light source. In some embodiments, the system further comprises a wavelength calibration source, the computing device further configured to receive a wavelength calibration signal measured by one or more of the imaging devices from the wavelength calibration source and to calculate a pixel to wavelength conversion for one or more spectral images from the corresponding wavelength calibration signal.

In some embodiments, at least one metric indicative of disease state is calculated for each pixel of at least one of the spectral or spatial images. In some embodiments, the computing device can be further configured to segment the spectral images into various components of the eye and calculate a metric indicative of a disease state for each component based on the averaged spectral data of that component. In some embodiments, the segmentation of the spectral image into components is performed by an automated segmentation algorithm. In some embodiments, a metric indicative of disease state is calculated based on a ratio of the metrics of disease state between different components. In some embodiments, the system further comprises a white reference light source and target to generate a white reference spectrum of the system. In some embodiments, the metric indicative of disease state is based on the optical density or the reflectance of the retina calculated relative to the white reference spectrum at one or more wavelengths or wavelength ranges. In some embodiments, the metric indicative of disease state is based on the ratios of the optical density or reflectance at two or more different wavelengths or wavelength ranges. In some embodiments, the wavelengths or wavelength ranges used to calculate the ratios are determined based on a statistical significance test performed on a database of corresponding values measured from subjects with known positive and negative disease state. In some embodiments, the computing device is further configured to extract features from one or more spatial images to calculate one or more spatial data metrics indicative of disease state based on the extracted features alone or in combination with the spectral data metrics. In some embodiments, the computing device is configured to use a first image to determine the most appropriate imaging device settings for producing a second image from the same or different imaging device. In some embodiments, the computing device is further configured to receive demographic or other medical information and calculate one or more further metrics of disease state based on the demographic or other medical information in combination with one or more spectral data or spatial data metrics.

In some embodiments, the computing device is further configured to calculate one or more quality assurance metrics for the spatial or spectral data and reject data, or portions of the data, in which the quality assurance metrics are above or below pre-set quality assurance thresholds. In some embodiments, the system further comprises one or more additional imaging devices such as optical coherence tomography, Raman spectroscopy, or other devices for measuring the fundus in one or more dimensions, the computing device further configured to calculate one or more additional metrics indicative of disease status based on the output of the imaging devices alone or in combination with the other calculated metrics of disease state. In some embodiments, the metrics of disease state are indicative of amyloid or tau status of the eye, or the absence, presence or progression of Alzheimer's disease or the risk of developing In some embodiments, the machine learning or artificial intelligence algorithms are based on one or more of logistic regression, decision tree, random forest, linear discriminant analysis, neural networks (including convolutional neural networks), naïve bayes classifier, nearest neighbor classifier or other ML or AI techniques.

Figure 18:
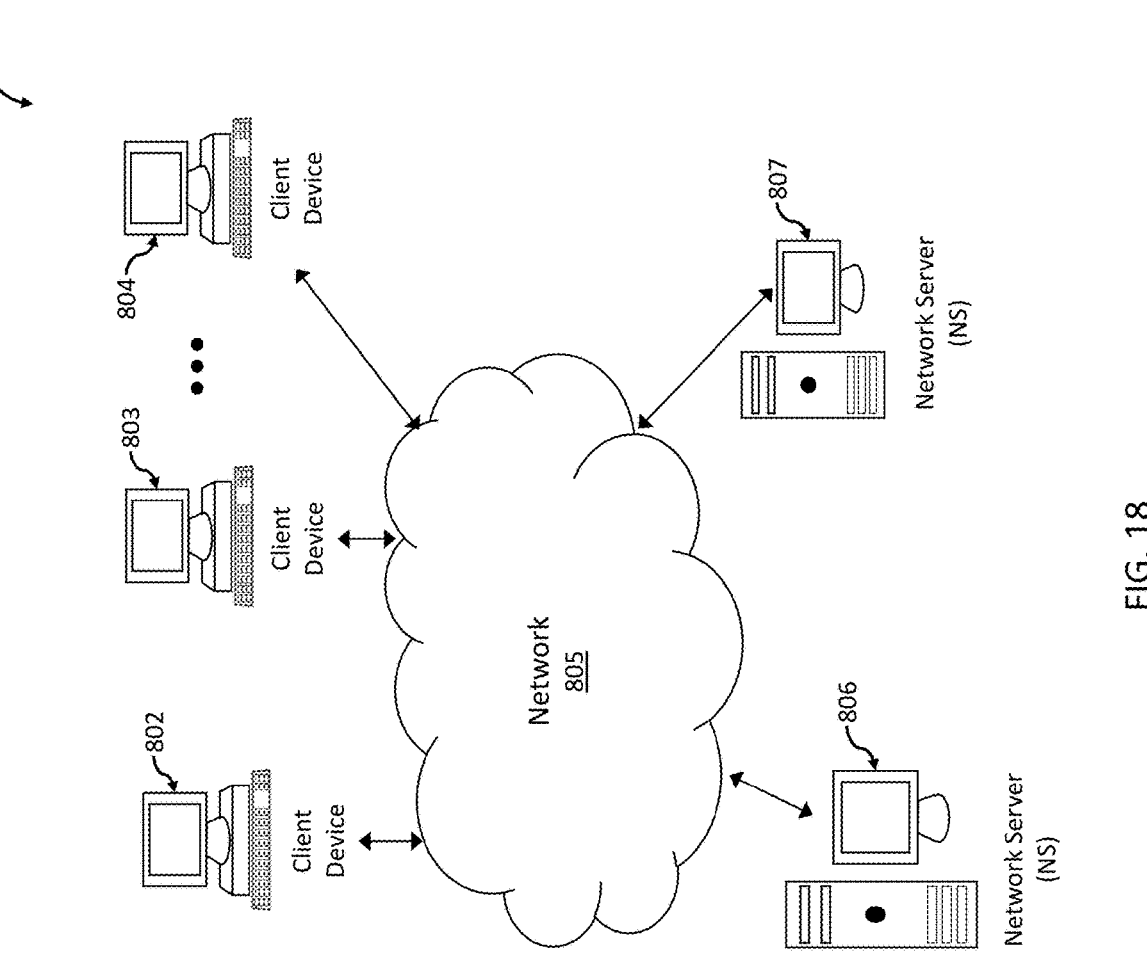
FIG. 18 depicts a block diagram of an exemplary computer-based system and platform.

FIG. 18 depicts a block diagram of an exemplary computer-based system and platform 800 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 800 may be configured to manage a large number of members and concurrent transactions, as detailed herein. In some embodiments, the exemplary computer-based system and platform 800 may be based on a scalable computer and network architecture that incorporates various strategies for assessing the data, caching, searching, and/or database connection pooling. An example of the scalable architecture is an architecture that is capable of operating multiple servers.

In some embodiments, referring to FIG. 18, member computing device 802, member computing device 803 through member computing device 804 (e.g., clients) of the exemplary computer-based system and platform 800 may include virtually any computing device capable of receiving and sending a message over a network (e.g., cloud network), such as network 805, to and from another computing device, such as servers 806 and 807, each other, and the like. In some embodiments, the member devices 802-804 may be personal computers, multiprocessor systems, microprocessor-based or programmable consumer electronics, network PCs, and the like. In some embodiments, one or more member devices within member devices 802-804 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 802-804 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 802-804 may include may run one or more applications, such as Internet browsers, mobile applications, voice calls, video games, videoconferencing, and email, among others. In some embodiments, one or more member devices within member devices 802-804 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 802-804 may be specifically programmed by either Java, .Net, QT, C, C++ and/or other suitable programming language. In some embodiments, one or more member devices within member devices 802-804 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 805 may provide network access, data transport and/or other services to any computing device coupled to it. In some embodiments, the exemplary network 805 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 805 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 805 may include and implement, as an alternative or in conjunction with one or more of the above, a WiMAX architecture defined by the WiMAX forum. In some embodiments and, optionally, in combination of any embodiment described above or below, the exemplary network 805 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 805 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 805 may also include mass storage, such as network attached storage (NAS), a storage area network (SAN), a content delivery network (CDN) or other forms of computer or machine readable media.

In some embodiments, the exemplary server 806 or the exemplary server 807 may be a web server (or a series of servers) running a network operating system, examples of which may include but are not limited to Microsoft Windows Server, Novell NetWare, or Linux. In some embodiments, the exemplary server 806 or the exemplary server 807 may be used for and/or provide cloud and/or network computing. Although not shown in FIG. 18, in some embodiments, the exemplary server 806 or the exemplary server 807 may have connections to external systems like email, SMS messaging, text messaging, ad content providers, etc. Any of the features of the exemplary server 806 may be also implemented in the exemplary server 807 and vice versa.

In some embodiments, one or more of the exemplary servers 806 and 807 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 801-804.

In some embodiments and, optionally, in combination of any embodiment described above or below, for example, one or more exemplary computing member devices 802-804, the exemplary server 806, and/or the exemplary server 807 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 19:
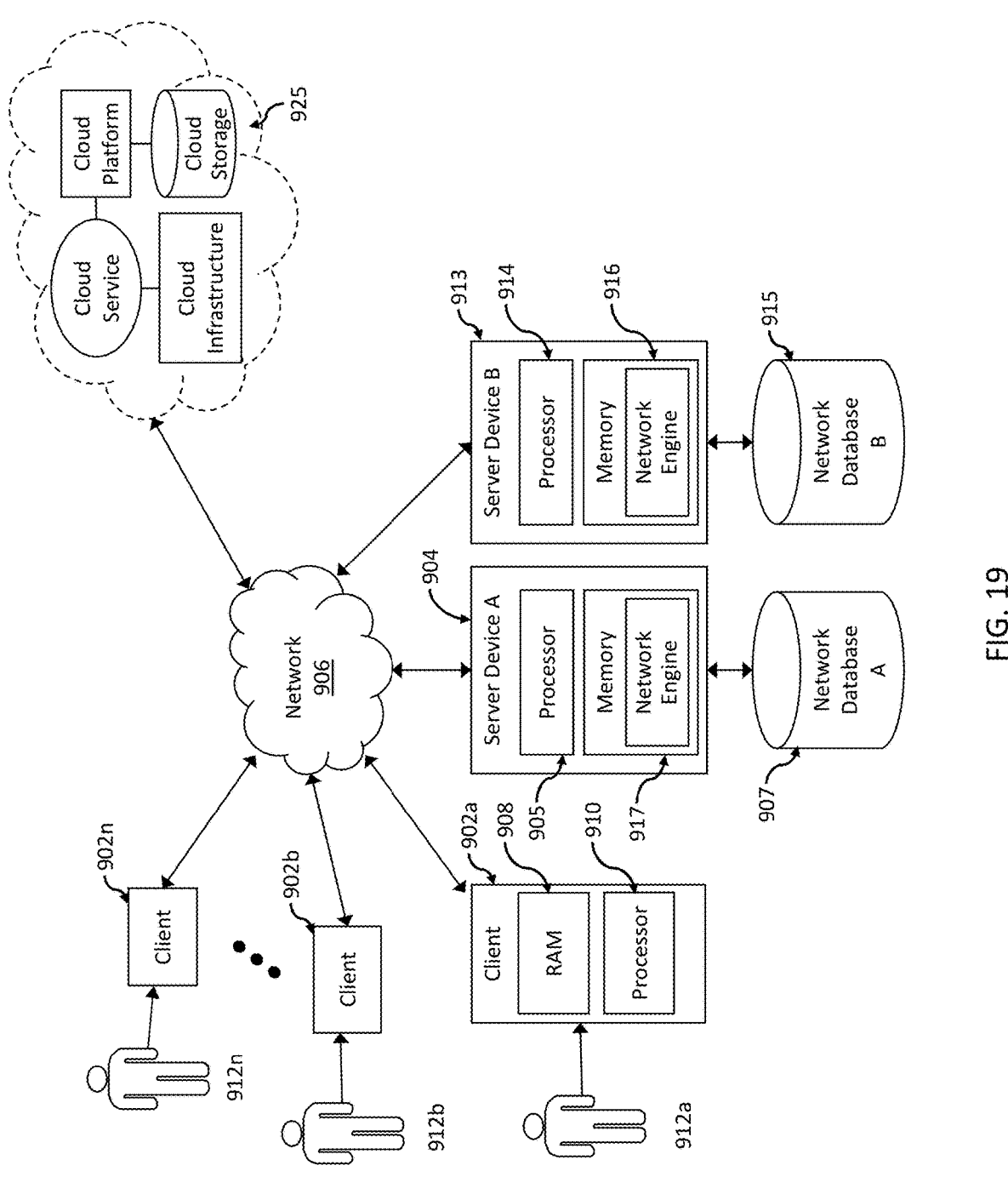
FIG. 19 depicts a block diagram of an exemplary computer-based system and platform.

FIG. 19 depicts a block diagram of another exemplary computer-based system and platform 900 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing device 902a, member computing device 902b through member computing device 902n shown each at least includes a computer-readable medium, such as a random-access memory (RAM) 908 coupled to a processor 910 or FLASH memory. In some embodiments, the processor 910 may execute computer-executable program instructions stored in memory 908. In some embodiments, the processor 910 may include a microprocessor, an ASIC, and/or a state machine. In some embodiments, the processor 910 may include, or may be in communication with, media, for example computer-readable media, which stores instructions that, when executed by the processor 910, may cause the processor 910 to perform one or more steps described herein. In some embodiments, examples of computer-readable media may include, but are not limited to, an electronic, optical, magnetic, or other storage or transmission device capable of providing a processor, such as the processor 910 of client 902a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 902a through 902n may also comprise a number of external or internal devices such as a mouse, a CD-ROM, DVD, a physical or virtual keyboard, a display, or other input or output devices. In some embodiments, examples of member computing devices 902a through 902n (e.g., clients) may be any type of processor-based platforms that are connected to a network 906 such as, without limitation, personal computers, digital assistants, personal digital assistants, smart phones, pagers, digital tablets, laptop computers, Internet appliances, and other processor-based devices. In some embodiments, member computing devices 902a through 902n may be specifically programmed with one or more application programs in accordance with one or more principles/methodologies detailed herein. In some embodiments, member computing devices 902a through 902n may operate on any operating system capable of supporting a browser or browser-enabled application, such as Microsoft™, Windows™, and/or Linux. In some embodiments, member computing devices 902a through 902n shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 902a through 902n, user 912a, user 912b through user 912n, may communicate over the exemplary network 906 with each other and/or with other systems and/or devices coupled to the network 906. As shown in FIG. 19, exemplary server devices 904 and 913 may include processor 905 and processor 914, respectively, as well as memory 917 and memory 916, respectively. In some embodiments, the server devices 904 and 913 may be also coupled to the network 906. In some embodiments, one or more member computing devices 902*a* through 902*n* may be mobile clients.

In some embodiments, at least one database of exemplary databases 907 and 915 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 20:
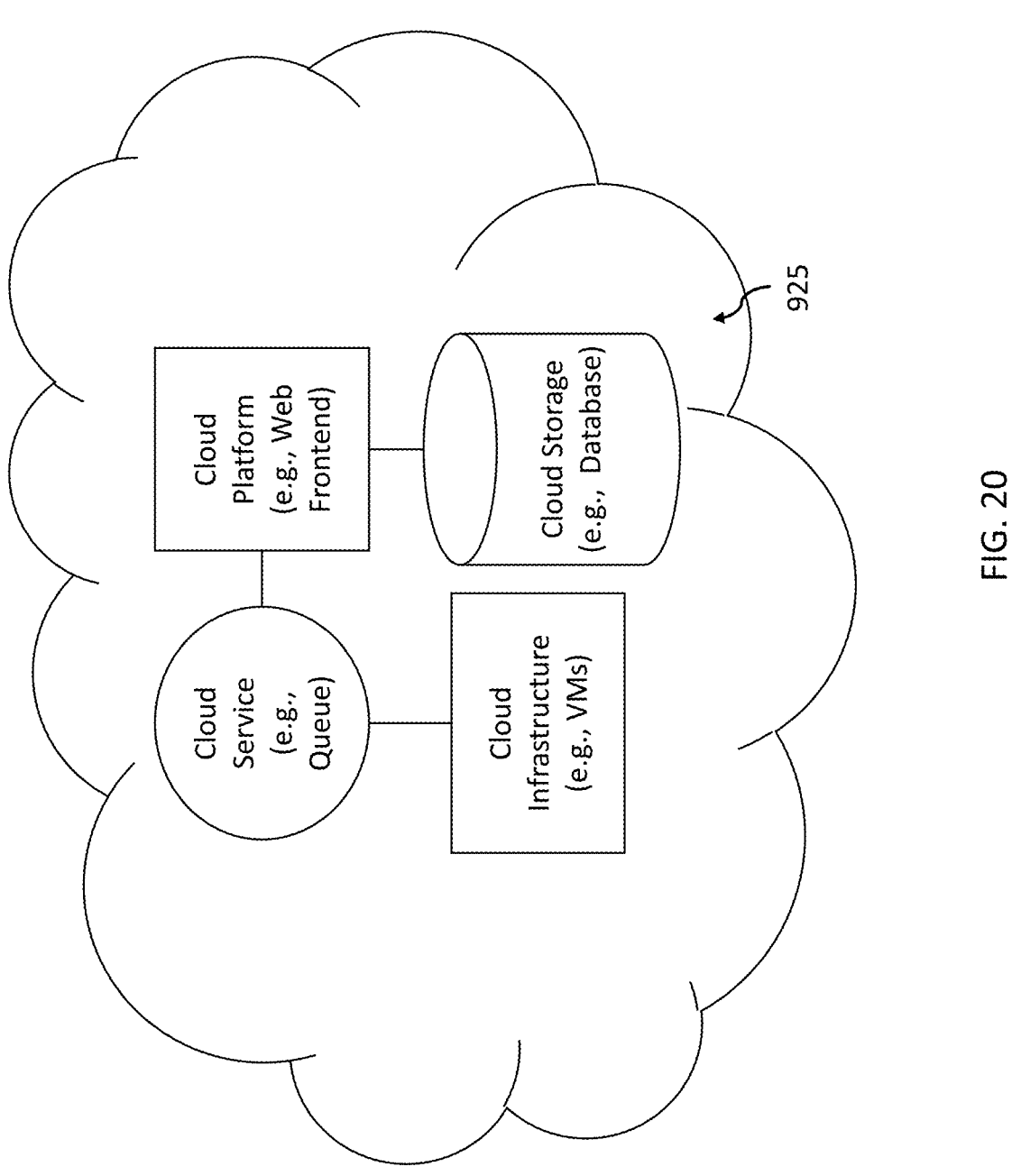
FIG. 20 illustrates a schematic of an exemplary implementation of a cloud computing/architecture.
Figure 21:
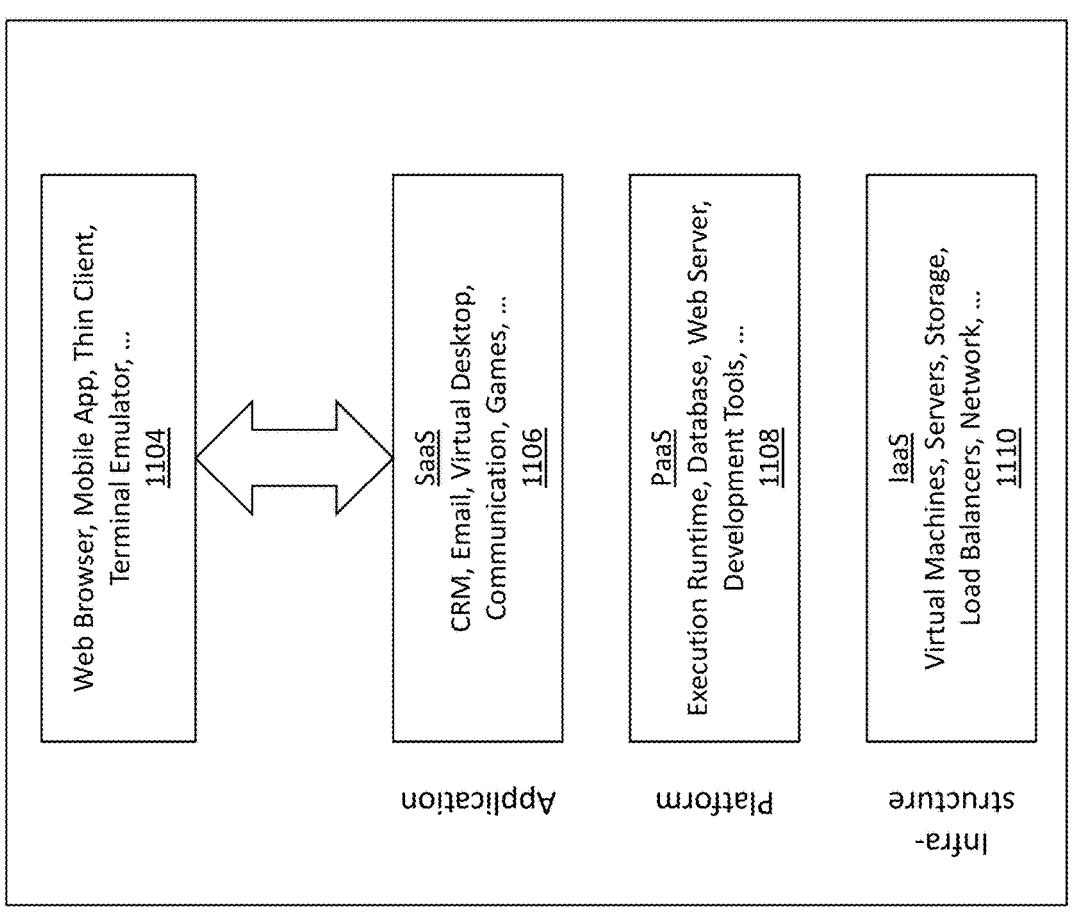
FIG. 21 illustrates a schematic of an exemplary implementation of a cloud computing/architecture.

In some embodiments, the exemplary inventive computer-based systems/platforms, the exemplary inventive computer-based devices, and/or the exemplary inventive computer-based components of the present disclosure may be specifically configured to operate in a cloud computing/architecture 925 such as, but not limiting to: infrastructure a service (IaaS) 1110, platform as a service (PaaS) 1108, and/or software as a service (SaaS) 1106 using a web browser, mobile app, thin client, terminal emulator or other endpoint 1104. FIGS. 20 and 21 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

In some embodiments, the pathology information of a patient can be compared to personal history of the same patient to see a progression (regression). The progression (regression) of the patient can also be compared to other population cohorts and their historical progression (regression).

The server can implement the machine learning algorithm by way of one or more neural networks. The machine learning algorithm can include logistic regression, variational autoencoding, convolutional neural networks, or other statistical techniques used to identify and discern neurogenerative disease-associated pathologies. The machine learning algorithm can also use spectral scattering models, other scattering models, or optical physics models that are validated a priori. The neural network may comprise a plurality of layers, some of which are defined and some of which are undefined (or hidden). The neural network is a supervised learning neural network.

In some examples, the neural network may include a neural network input layer, one or more neural network middle hidden layers, and a neural network output layer. Each of the neural network layers include a plurality of nodes (or neurons). The nodes of the neural network layers are connected, typically in series. The output of each node in a given neural network layer is connected to the input of one or more nodes in a subsequent neural network layer. Each node is a logical programming unit that performs an activation function (also known as a transfer function) for transforming or manipulating data based on its inputs, a weight (if any) and bias factor(s) (if any) to generate an output. The activation function of each node results in a particular output in response to particular input(s), weight(s) and bias factor(s). The inputs of each node may be scalar, vectors, matrices, objects, data structures and/or other items or references thereto. Each node may store its respective activation function, weight (if any) and bias factors (if any) independent of other nodes. In some example embodiments, the decision of one or more output nodes of the neural network output layer can be calculated or determined using a scoring function and/or decision tree function, using the previously determined weight and bias factors, as is understood in the art.

In some examples, the classification (output of the second neural network) can be one or more conclusions as to whether the subject has a neurogenerative pathology, or a precursor to a neurogenerative pathology, or is pre-screened for potential of neurogenerative pathology and requires further investigation. Such neurogenerative pathology conclusions can be based on one or a plurality of pathologies that are classified by the neural network, and determined or calculated using e.g. a combined weighted score, scorecard, or probabilistic determination. For example, the presence or probabilistic classification of both Amyloid Beta and Tau neurofibrillary tangles may lead to a higher probability conclusion of a neurogenerative pathology. In some examples, the conclusions can also be based on the changes over time of the patient physiology, for example by comparing with previous spectroscopy information of the patient. In some examples, the hyperspectral reflectance information is also used as input information to the neural network, which further assists in classifying neurogenerative pathologies.

From the foregoing description, it will be apparent that variations and modifications may be made to the embodiments of the present disclosure to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:

1. An imaging system comprising:
   a light source configured to illuminate a retina of an eye with light;

one or more imaging devices configured to receive light returned from the retina to generate one or more spatial-spectral images of the retina; and a computing device configured to receive the one or more spatial-spectral images of the retina, extract segmented vessels of the retina from the one or more spatial-spectral images, evaluate the segmented vessels of the one or more spatial-spectral images, and identify one or more biomarkers indicative of a neurogenerative pathology along the segmented vessels or walls of the segmented vessels.

2. The imaging system of claim 1, wherein the one or more imaging devices comprise a spectral sensor, wherein the spectral sensor comprises a hyperspectral sensor or multispectral sensor.

3. The imaging system of claim 1, wherein the neurogenerative pathology is selected from a group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), and cerebral amyloid angiopathy (CAA).

4. The imaging system of claim 1, wherein the one or more biomarkers comprise Amyloid or Tau protein formations.

5. The imaging system of claim 1 further comprising a retinal viewing device, wherein the one or more imaging devices and the light source are integrated into the retinal viewing device.

6. The imaging system of claim 1, wherein the one or more spatial-spectral images comprise spectral images of multiple retinal regions;

wherein, for each of the multiple retinal regions, the one or more spatial-spectral images comprise spectral images at multiple wavelength ranges; and wherein the spectral images comprise spatial information about a corresponding retinal region, wherein the spatial information comprises at least one of texture, formations and patterns in the corresponding retinal region.

7. The imaging system of claim 1, wherein the evaluation of the one or more spatial-spectral images uses a pixel-wise analysis of the one or more spatial-spectral images.

8. The imaging system of claim 1, wherein the computing device is further configured to output two probability maps indicating the segmented vessels of the retina, wherein a first probability map is for arteries, and a second probability map is for veins.

9. The imaging system of claim 1, wherein the computing device is further configured to analyze a structure of the segmented vessels and as a spectral signature along the segmented vessels to detect the one or more biomarkers indicative of the neurogenerative pathology.

10. An imaging system comprising:

a light source configured to illuminate a retina of an eye with light;

one or more imaging devices configured to receive light returned from the retina to generate at least one spectral image and at least one spatial image of the retina; and a computing device configured to receive the at least one spectral image and at least one spatial image of the retina, extract segmented vessels of the retina from the at least one spectral image and at least one spatial image, evaluate the segmented vessels of the at least one spectral image and at least one spatial image, and identify one or more biomarkers indicative of a neurogenerative disease along the segmented vessels or walls of the segmented vessels.

11. The imaging system of claim 10, wherein the one or more imaging devices comprises a spatial camera configured to generate the at least one spatial image and a hyperspectral camera configured to generate the at least one spectral image.

12. The imaging system of claim 10, wherein the one or more imaging devices comprises a hyperspectral camera configured to generate an image that includes the at least one spectral image and the at least one spatial image.

13. The imaging system of claim 10, wherein the one or more biomarkers comprise Amyloid or Tau protein formations.

14. A method for diagnosing a neurogenerative disease comprising: illuminating a retina of an eye with light with a light source;

generating at least one spatial-spectral image by one or more imaging devices, the one or more imaging devices configured to receive light returned from the retina;

extracting segmented vessels of the retina from the at least one spatial-spectral image;

evaluating the segmented vessels of the at least one spatial-spectral image, the segmented vessels of the at least one spatial-spectral image being evaluated by a computing device configured to receive the at least one spatial-spectral image from the one or more imaging devices; and identifying one or more biomarkers indicative of a neurogenerative disease.

15. The method of claim 14, wherein the evaluation of the at least one spatial-spectral image uses a pixel-wise analysis of the at least one spatial-spectral image.

16. The method of claim 14, wherein the one or more imaging devices comprise a spectral sensor, wherein the spectral sensor comprises a hyperspectral sensor or multispectral sensor.

17. The method of claim 14, wherein the neurogenerative disease is selected from a group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), and cerebral amyloid angiopathy (CAA).

18. The method of claim 14, wherein the one or more biomarkers comprise Amyloid or Tau protein formations.

19. A method for diagnosing a neurogenerative disease comprising:

obtaining, by a computer device, a retinal image mosaic comprising a plurality of spatial-spectral images from one or more regions of a retina;

analyzing, by the computer device, the retinal image mosaic to extract segmented vessels of the retina from the plurality of spatial-spectral images;

identify, from the segmented vessels, one or more biomarkers indicative of a neurogenerative pathology along the segmented vessels or walls of the segmented vessels; and generating, by the computer device, a digital representation indicative of a presence or absence of the one or more biomarkers in the one or more regions of a retina.

20. The method of claim 19, further comprising predicting a probability of the neurogenerative pathology from the digital representation.

21. The method of claim 19, wherein the digital representation is a heat map overlaid on the retinal image mosaic or on the segmented vessels.

22. The method of claim 19, wherein analyzing the plurality of spatial-spectral images comprises using a pixel-wise analysis of each image.

23. The method of claim 19, wherein the plurality of spatial-spectral images are generated by one or more imaging devices comprise a spectral sensor, wherein the spectral sensor comprises a hyperspectral sensor or multispectral sensor.

24. The method of claim 19, wherein the neurogenerative pathology is selected from a group consisting of Alzheimer's disease, Parkinson's disease, Amyotrophic Lateral Sclerosis, Multiple Sclerosis, Prion disease, Motor neurone diseases (MND), Huntington's disease (HD), Spinocerebellar ataxia (SCA), Spinal muscular atrophy (SMA), and cerebral amyloid angiopathy (CAA).

25. The method of claim 19, wherein the one or more biomarkers comprise Amyloid or Tau protein formations.

26. An imaging system comprising:

a light source configured to illuminate a retina of an eye with light;

one or more imaging devices configured to receive light returned from the retina to generate one or more spatial-spectral images of the retina; and a computing device configured to obtain a retinal image mosaic comprising the one or more spatial-spectral images from one or more regions of a retina, analyze the retinal image mosaic to extract segmented vessels of the retina from the one or more spatial-spectral images, identify, from the segmented vessels, one or more biomarkers indicative of a neurogenerative pathology, and generate a digital representation indicative of a presence or absence of the one or more biomarkers in the one or more regions of a retina.

\* \* \* \* \*